US010323002B2

(12) United States Patent
Broggini et al.

(10) Patent No.: US 10,323,002 B2
(45) Date of Patent: *Jun. 18, 2019

(54) PROCESS FOR THE PREPARATION OF HISTAMINE H3 RECEPTOR MODULATORS

(71) Applicant: Janssen Pharmaceutica NV, Beerse (BE)

(72) Inventors: Diego Fernando Domenico Broggini, Zurich (CH); Vit Lellek, Zurich (CH); Susanne Lochner, Singen (DE); Neelakandha S. Mani, San Diego, CA (US); Adrian Maurer, Schaffhausen (CH); Daniel J. Pippel, Del Mar, CA (US); Lana K. Young, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,711

(22) Filed: Oct. 4, 2017

(65) Prior Publication Data
US 2018/0022704 A1    Jan. 25, 2018

Related U.S. Application Data

(60) Continuation of application No. 15/349,521, filed on Nov. 11, 2016, now Pat. No. 9,809,547, which is a division of application No. 14/261,713, filed on Apr. 25, 2014, now Pat. No. 9,518,021, which is a division of application No. 13/257,224, filed as application No. PCT/US2010/027638 on Mar. 17, 2010, now Pat. No. 8,748,596.

(60) Provisional application No. 61/161,177, filed on Mar. 18, 2009.

(51) Int. Cl.
| C07D 401/06 | (2006.01) |
| C07D 401/14 | (2006.01) |
| C07D 213/82 | (2006.01) |
| C07D 405/12 | (2006.01) |

(52) U.S. Cl.
CPC ......... *C07D 213/82* (2013.01); *C07D 405/12* (2013.01); *C07B 2200/13* (2013.01)

(58) Field of Classification Search
CPC ............................ C07D 401/06; C07D 401/14
See application file for complete search history.

(56) References Cited

U.S. PATENT DOCUMENTS

| 8,748,596 | B2 | 6/2014 | Broggini et al. |
| 8,883,776 | B2 | 11/2014 | Letavic et al. |
| 9,518,021 | B2 | 12/2016 | Broggini et al. |
| 2007/0281923 | A1 | 12/2007 | Keith et al. |
| 2009/0131415 | A1 | 5/2009 | Letavic et al. |
| 2017/0057919 | A1 | 3/2017 | Broggini et al. |

FOREIGN PATENT DOCUMENTS

| WO | WO 2007 143422 A2 | 12/2007 |
| WO | WO 2009 067401 A1 | 5/2009 |

OTHER PUBLICATIONS

Anderson et al., "NMR Study of Stereoelectric Anomeric and Homoanomeric Effects on the Axial and Equatorial CH Bonds in 1,3-Diazacyclohexanes and 1,-5-Diazabicyclo[3.2.1]Octanes" Journal of Chemical Society Perkin Trans, (1997), vol. 2 (12) pp. 2633-2637.
Arrang et al., "Auto-Inhibition of Brain Histamine Release Mediated by a Novel Class (H3) of Histamine Receptor", Nature (1983), vol. 302, pp. 832-837.
Bagshawe et al., "Antibody-Directed Enzyme Prodrug Therapy: A Review", Drug Dev Res, (1995), vol. 35, pp. 220-230.
Barnes, et al., "The Selective Histamine H3 Recptors Antagonist Thioperamide Improves Cognition and Enhances Hippocampal Acetylcholine Release In Vivo", Soc Neurosci Abstr, (1993), vol. 19, pp. 1813.
Berge, et al., "Pharmaceutical Salts", J. Pharm. Sci. (1977), vol. 66, pp. 1-19.
Bertolini, et al., "A New Rational Hypothesis for the Pharmacophore of the Active Metabolite of Leflunomide, A Potent Immunosuppressive Drug", J. Med. Chem. (1997), vol. 40, pp. 2011-2016.
Bodor, et al., "Novel Approaches to the Design of Safer Drugs: Soft Drug and Site-Specific Chemical Delivery System", Adv. Drugs Res. (1984), vol. 13, pp. 224-331.
Bonaventure, et al., "Histamine H3 Receptor Antagonists: Form Target Identification to Drug Leads", Biochem Pharm, (2007), vol. 73, pp. 1084-1096.
Boyd, E. et al., "Synthesis and Derivatisation of N,N'-Trisubstituted 1,2-Diamines Derived From (1R, 2R)-1,2-Diamioncyclohexane", Tetrahedron Letters, (2005), vol. 46, No. 20, pp. 3479-3484.
Bundgaard et al., Design of Prodrugs 1985 Eds H. Hundgaard Elsevier.
Chen et al., "Effects of Histamine H3-Receptor Antagonist Clobenpropit on Spatial Memory of Radial Maze Performance in Rats", Acta Pharmacol Sin, (2000), vol. 21, No. 10, pp. 905-910.
Fleisher et al., "Improved Oral Drug Delivery: Solubility Limitations Overcome by the Use of Prodrugs", Adv Drug Delivery Rev, (1996), vol. 19, pp. 115-130.
Fox et al., "Effects of Histamine H3 Receptor Ligands GT-2331 and Ciproxifan in a Repeated Acquisition Avoidance Response in the Spotaneously Hypertensive Rat Pup", Behav Brain Res, (2002), vol. 131, No. 1-2, pp. 151-161.
Greene et al., "Protective Groups in Organic Synthesis TW Green and PGM WUTS", John Wiley and Sons (1991).
The Handbook of Pharmaceutical Excipients American Pharmaceutical Association and the Pharmaceutical Association of Great Britain Publishers (2009).
Kalyanam et al., "Stereochemistry and Conformation of 8-ARYL-1,5-Diazabicyclo[3.2.1] Octanes by 2D NMR Studies" Journal of Organic Chemistry, (1988) vol. 53, pp. 422.

(Continued)

*Primary Examiner* — Brenda L Coleman
(74) *Attorney, Agent, or Firm* — Scully Scott Murphy & Presser

(57) ABSTRACT

The present invention is directed to novel processes for the preparation of histamine H3 receptor modulators, in the treatment of for example, cognitive disorders, sleep disorders and/or psychiatric disorders.

2 Claims, 3 Drawing Sheets

(56) References Cited

OTHER PUBLICATIONS

Krause et al. & Phillips et al., "The Histamine H3 Receptor—Targed for New Drugs" Leurs R and Timmerman H. Eds, (1998), pp. 175-196 and 197-222.
Lamberti et al., "Antidepressant-Like Effects of Endogenous Histamine and of Two Histamine H1 Receptor Agonists in the Mouse Forced Swim Test" Br. J. Pharmacol., (1998), vol. 123, No. 7, pp. 1331-1336.
Larsen et al., Drug Design and Development Krogsgaar-Larsen et al. Eds Hardwood Academic Publihshers 1991.
Letavic et al., "5 Recent Medicinal Chemistry of the Histamine H3 Receptor" Prog Med Chem 1996 vol. 44 pp. 181-206.
Leurs et al., "The Medicinal Chemistry and Therapeutic Potentials of Ligands of the Histamine H3 Receptor", Prog Drug Res 1995 vol. 45 pp. 107-165.
Machidori et al., "Zucker Obsese Rats: Defect in Brain Histamine Control of Feeding" Brain Res 1992 vol. 590 pp. 180-186.
Mcomie et al. Protective Groups in Organic Chemistry Ed JFW Mcomie Plenum Press 1973.
Miyazaki et al "Effects of Thioperamide a Histamine H3-Receptor Antagonist on a Scopolamine-Induced Learning Deficit Using an Elevated Pluz-Maze Test in Mice" Life Sci 1995 vol. 57(23) pp. 2137-2144.
Miyazaki et al., "Effects of Thioperamide on the Cholinergic System and the Step-Trhough Passive Avoidance Test in Mice", Meth Find Exp Clin Pharmacol 1995 vol. 17(10) pp. 653-658.
Morisset et al "High Constitutive Activity of Native H3 Receptors Regulates Histamine Neurons in Brain" Nature 2000 vol. 408 pp. 860-864.
Orsetti et al. "Histamine H3-Receptor Antagonism Improves Memory Retention and Reverses the Cognitive Deficit Induced by Scopolamine in a Two Trial Place Recognition Task" Behav Brain Res 2001 vol. 124(2) pp. 235-242.
Panula et al. "Significant Changes in the Human Brain Histaminergic System in Alzheimer's Disease", Soc Neurosci Abstr 1995 vol. 21 pp. 1977.
Perez Garcia et al., "Effects of Histamine H3 Receptor Ligands in Experimental Models of Anxiety and Depression" Psychopharmacology, 1999, vol. 142(2), pp. 215-220.
Pharmaceutical Dosage Forms Tablets Second Ed Revised and Expanded, 1990, vols. 1-3 Edited by Lieberman et al.
Pharmaceutical Dosage Forms Parenteral Medications, 1996, vols. 1-2, Edited by Avis et al.
Pharmaceutical Dosage Forms Disperse Systems, 1996, vol. 1-2 Eidted by Lieberman et al. Published by Marcel Dekker Inc.
Robinson et al. "Discovery of the Hemifumarate and (A-L-Alanyloxy)Methyl Ether as Prodrugs of an Antirheumatic Oxindole: Prodrugs of the Enolic OH Group" J Med Chem 1996 vol. 39 pp. 10-18.
Schlicker et al. "The Moderate Afffinity of Clozapine at H3 Receptors is not Shared by its Two Major Metabolites and by Structurally Related and Unrelated Atypical Neuroleptics" Naunyn-Schmiedeberg's Arch Pharmacol 1996 vol. 353 pp. 290-294.
Shan et al., "Prodrug Strategies Based on Intromolecular Cyclization Reactions" J Pharm Sci 1997 vol. 86(7) pp. 765-767.
Stahl et al. Handbook of Pharmaceutical Salts, Properties, Selection and Use Stahl and Wurmuth Eds Wiley-VCH and VHCA Zurich 2002.
Stark et al. "Development of Histamine H3-Receptor Antagonists" Drugs Future 1996, vol. 21(5) pp. 507-520.
Yokoyama et al., "Effects of Thioperaminde, A Histamine H3 Receptor Antagonist on Electrically Induced Convulsions in Mice" Eur J Pharmacol 1993 vol. 234 pp. 129-133.
International Search Report for corresponding International Publication PCT/US2010/27638 dated Mar. 3, 2011.

Representative Powder XRD Spectra for Crystalline HCl salt of Compound of Compound (I-B),FORM I Representative Powder XRD Spectra for Crystalline HCl salt of Compound of Compound (I-B), FORM II

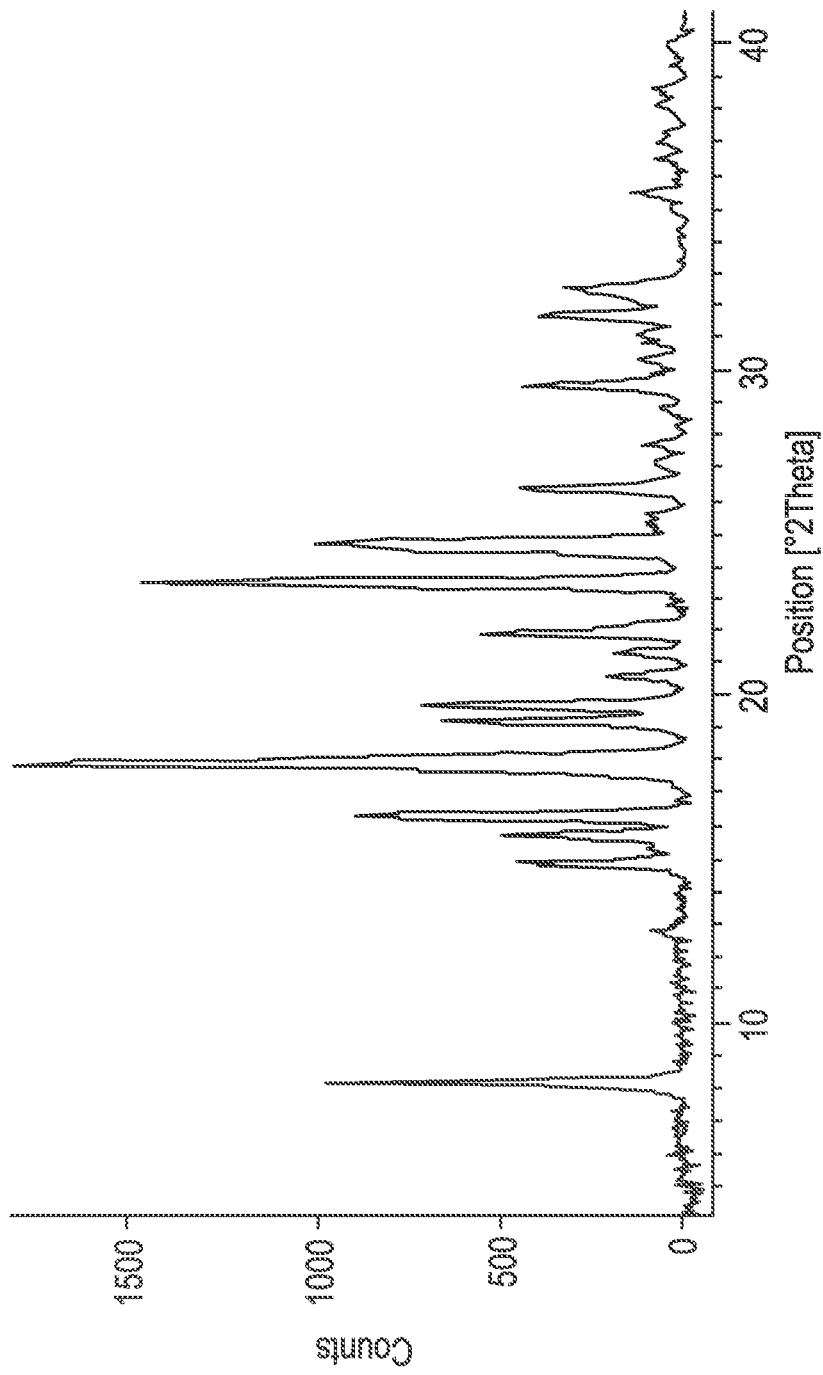

PROCESS FOR THE PREPARATION OF HISTAMINE H3 RECEPTOR MODULATORS

CROSS REFERENCE TO RELATED APPLICATIONS

The present application is a continuation of U.S. application Ser. No. 15/349,521, filed on Nov. 11, 2016, now U.S. Pat. No. 9,809,547, which is a divisional of U.S. application Ser. No. 14/261,713, filed on Apr. 25, 2014, now U.S. Pat. No. 9,518,021, which is a divisional of U.S. application Ser. No. 13/257,224, filed on Sep. 16, 2011, now U.S. Pat. No. 8,748,596, which is a National Phase of PCT/US2010/027638 filed on Mar. 17, 2010, which claims priority to U.S. Provisional Application No. 61/161,177, filed on Mar. 18, 2009, which is herein incorporated by reference in its entirety.

FIELD OF THE INVENTION

The present invention is directed to novel processes for the preparation of histamine H3 receptor modulators, in the treatment of for example, cognitive disorders, sleep disorders and/or psychiatric disorders.

BACKGROUND OF THE INVENTION

The histamine $H_3$ receptor was first described as a presynaptic autoreceptor in the central nervous system (CNS) (ARRANG, J.-M. et al., "Auto-inhibition of brain histamine release mediated by a novel class ($H_3$) of histamine receptor", *Nature*, 1983, pp 832-837, vol. 302) controlling the synthesis and release of histamine. The histamine $H_3$ receptor is primarily expressed in the mammalian central nervous system (CNS), with some minimal expression in peripheral tissues such as vascular smooth muscle.

Thus, several indications for histamine $H_3$ antagonists and inverse agonists have been proposed based on animal pharmacology and other experiments with known histamine $H_3$ antagonists (e.g. thioperamide). (See: KRAUSE, M., et al., "*The Histamine $H_3$ Receptor-A Target for New Drugs*, Leurs, R., et al. (Editors), Elsevier, 1998, pp 175-196 and pp 197-222; MORISSET, S. et al., "High constitutive activity of native $H_3$ receptors regulates histamine neurons in brain", *Nature*, 2000, pp 860-864, vol. 408) These include conditions such as cognitive disorders, sleep disorders, psychiatric disorders, and other disorders.

For example, histamine $H_3$ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. For reviews, see: BONAVENTURE, P. et al., "Histamine $H_3$ receptor antagonists: From target identification to drug leads" *Biochem. Pharm.*, 2007, pp 1084-1096, vol. 73; and LETAVIC, M. A. et al., "5 Recent Medicinal Chemistry of the Histamine $H_3$ Receptor", *Prog. Med. Chem.*, 2006, pp 181-206, vol. 44. There remains a need for potent histamine $H_3$ receptor modulators with desirable pharmaceutical properties.

Keith, J. M. et al., in US Patent Publication 2007/0281923-A1, published Dec. 6, 2007 disclose pyridyl amide compounds, methods of making them, pharmaceutical compositions containing them, and methods of using them for the treatment of disease states, disorders, and conditions mediated by the histamine $H_3$ receptor.

Letavic, M., et al., in U.S. Patent Publication 2009/0131415 A1, published May 17, 2009 disclose cycloalkyloxy- and heterocycloalkyloxypyridine compounds, methods of making them, pharmaceutical compositions containing them, and methods of using them for the treatment of disease states, disorders, and conditions mediated by the histamine $H_3$ receptor.

SUMMARY OF THE INVENTION

The present invention is directed to processes for the preparation of compounds of formula (I)

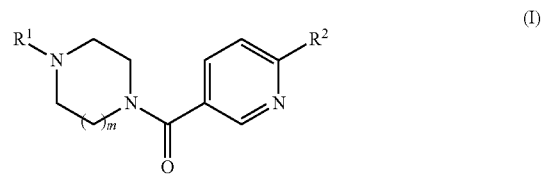

wherein
$R^1$ is selected from the group consisting of $C_{1-4}$alkyl and $C_{3-10}$cycloalkyl;
m is an integer from 1 to 2;
$R^2$ is selected from the group consisting of —OCHR$^3$R$^4$ and —Z—Ar;
$R^3$ is hydrogen and $R^4$ is a $C_{3-10}$cycloalkyl or heterocycloalkyl ring; wherein the $C_{3-10}$cycloalkyl or the heterocycloalkyl ring is unsubstituted or substituted with —$C_{1-4}$alkyl or acetyl;
alternatively, $R^3$ and $R^4$ are taken together with the carbon to which they are attached to form a $C_{3-10}$cycloalkyl or heterocycloalkyl ring; wherein the $C_{3-10}$ cycloalkyl or the heterocycloalkyl ring is unsubstituted or substituted with —$C_{1-4}$alkyl or acetyl;
Z is selected from the group consisting of S and O;
Ar is a phenyl or heteroaryl; wherein the phenyl or heteroaryl is unsubstituted or substituted with one, two, or three $R^5$ substituents; wherein each $R^5$ substituent is independently selected from the group consisting of halogen, —$C_{1-4}$alkyl, —OH, —OC$_{1-4}$alkyl, —SC$_{1-4}$alkyl, —CN, —CONR$^a$R$^b$, and —NO$_2$; and wherein $R^a$ and $R^b$ are each independently —H or —$C_{1-4}$alkyl;
or a pharmaceutically acceptable salt, a pharmaceutically acceptable prodrug, or a pharmaceutically active metabolite thereof; comprising

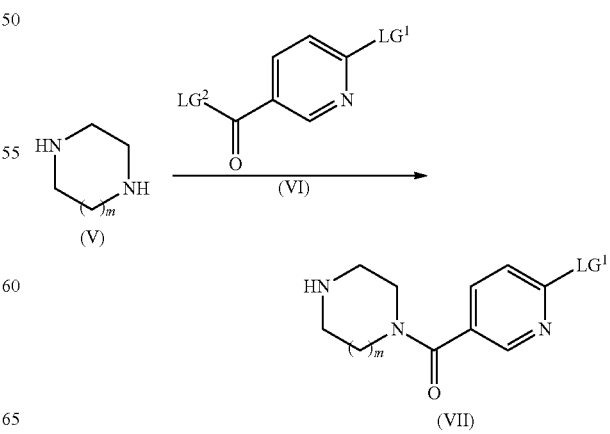

reacting a compound of formula (V) with a compound of formula (VI), wherein $LG^1$ is a first leaving group and $LG^2$ is a second leaving group, in the presence of a base, in an organic solvent; to yield the corresponding compound of formula (VII);

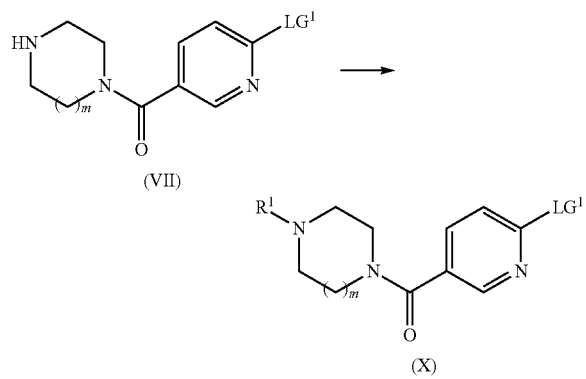

reacting the compound of formula (VII) with an aldehyde or ketone derivative of the desired $R^1$ substituent group; in the presence of a reducing agent; in an organic solvent; to yield the corresponding compound of formula (X);

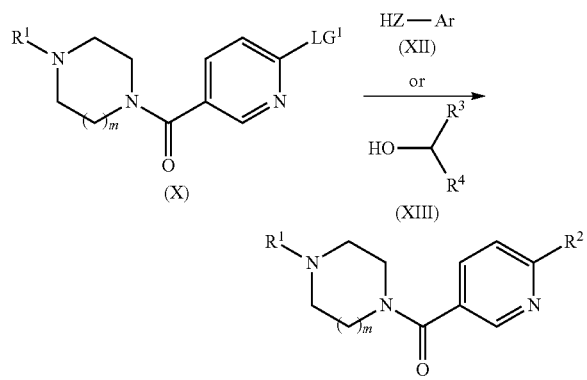

reacting the compound of formula (X) with a compound of formula (XII); in the presence of a first inorganic base; in an organic solvent; or reacting the compound of formula (X) with a compound of formula (XIII); in the presence of a second inorganic base; in an organic solvent;

to yield the corresponding compound of formula (I).

The present invention is directed to processes for the preparation of compounds of formula (I-E)

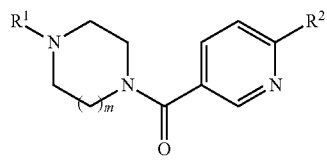

wherein $R^1$ is selected from the group consisting of $C_{1-4}$alkyl and $C_{3-10}$cycloalkyl;

m is 2

$R^2$ is selected from the group consisting of —OCHR$^3$R$^4$ and —Z—Ar;

$R^3$ is hydrogen and $R^4$ is a $C_{3-10}$cycloalkyl or heterocycloalkyl ring; wherein the $C_{3-10}$cycloalkyl or the heterocycloalkyl ring is unsubstituted or substituted with —$C_{1-4}$alkyl or acetyl;

alternatively, $R^3$ and $R^4$ are taken together with the carbon to which they are attached to form a $C_{3-10}$cycloalkyl or heterocycloalkyl ring; wherein the $C_{3-10}$ cycloalkyl or the heterocycloalkyl ring is unsubstituted or substituted with —$C_{1-4}$alkyl or acetyl;

Z is selected from the group consisting of S and O;

Ar is a phenyl or heteroaryl; wherein the phenyl or heteroaryl is unsubstituted or substituted with one, two, or three $R^5$ substituents; wherein each $R^5$ substituent is independently selected from the group consisting of halogen, —$C_{1-4}$alkyl, —OH, —O$C_{1-4}$alkyl, —S$C_{1-4}$alkyl, —CN, —CONR$^a$R$^b$, and —NO$_2$; and wherein R$^a$ and R$^b$ are each independently —H or —$C_{1-4}$alkyl;

or a pharmaceutically acceptable salt, a pharmaceutically acceptable prodrug, or a pharmaceutically active metabolite thereof; comprising

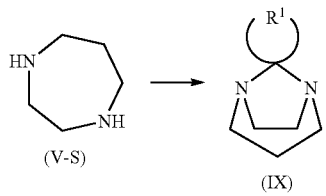

reacting a compound of formula (V-S) with an aldehyde or ketone derivative of the desired $R^1$ substituent group; neat or in an organic solvent; to yield the corresponding compound of formula (IX);

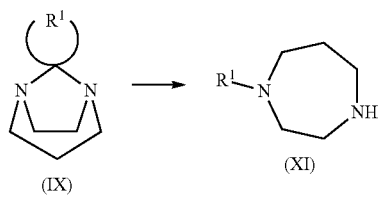

reacting the compound of formula (IX) with a reducing agent; neat, in water or an aqueous organic solvent; to yield the corresponding compound of formula (XI);

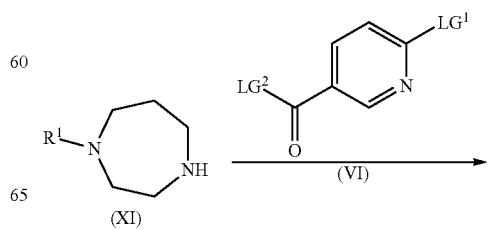

-continued

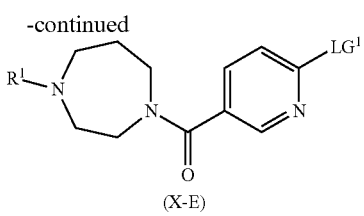

reacting the compound of formula (XI) with a compound of formula (VI), wherein $LG^1$ is a first leaving group and $LG^2$ is a second leaving group; in an organic solvent;

alternatively reacting the compound of formula (XI) with a compound of formula (VI), wherein $LG^1$ is a first leaving group and $LG^2$ is a second leaving group; in the presence of a base; in a mixture of water and an organic solvent;

solvent or mixture of solvents;

to yield the corresponding compound of formula (X-E)

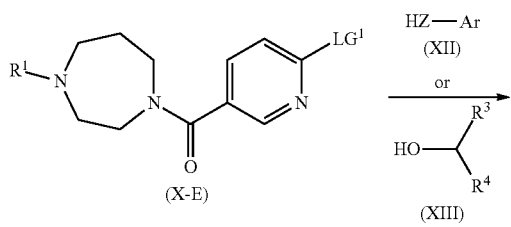

reacting the compound of formula (X-E) with a compound of formula (XII); in the presence of a first inorganic base; in an organic solvent; or reacting the compound of formula (X-E) with a compound of formula (XIII); in the presence of a second inorganic base; in an organic solvent;

to yield the corresponding compound of formula (I-E).

The present invention is directed to processes for the preparation of compounds of formula (I-E)

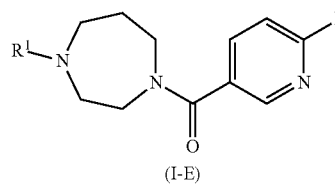

wherein $R^1$ is selected from the group consisting of $C_{1-4}$alkyl and $C_{3-10}$cycloalkyl;

m is 2

$R^2$ is selected from the group consisting of —OCHR$^3$R$^4$ and —Z—Ar;

$R^3$ is hydrogen and $R^4$ is a $C_{3-10}$cycloalkyl or heterocycloalkyl ring; wherein the $C_{3-10}$cycloalkyl or the heterocycloalkyl ring is unsubstituted or substituted with —$C_{1-4}$alkyl or acetyl;

alternatively, $R^3$ and $R^4$ are taken together with the carbon to which they are attached to form a $C_{3-10}$cycloalkyl or heterocycloalkyl ring; wherein the $C_{3-10}$cycloalkyl or the heterocycloalkyl ring is unsubstituted or substituted with —$C_{1-4}$alkyl or acetyl;

Z is selected from the group consisting of S and O;

Ar is a phenyl or heteroaryl; wherein the phenyl or heteroaryl is unsubstituted or substituted with one, two, or three $R^5$ substituents; wherein each $R^5$ substituent is independently selected from the group consisting of halogen, —$C_{1-4}$alkyl, —OH, —$OC_{1-4}$alkyl, —$SC_{1-4}$alkyl, —CN, —CONR$^a$R$^b$, and —NO$_2$; and wherein R$^a$ and R$^b$ are each independently —H or —$C_{1-4}$alkyl;

or a pharmaceutically acceptable salt, a pharmaceutically acceptable prodrug, or a pharmaceutically active metabolite thereof; comprising

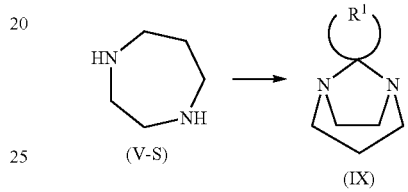

reacting a compound of formula (V-S) with an aldehyde or ketone derivative of the desired $R^1$ substituent group; neat or in an organic solvent; to yield the corresponding compound of formula (IX);

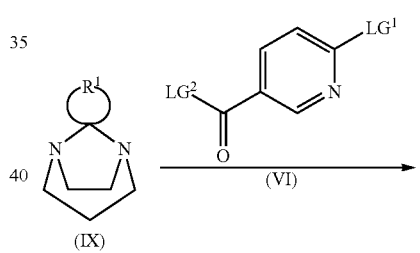

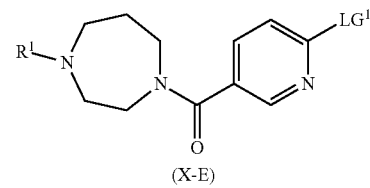

reacting the compound of formula (IX) with a compound of formula (VI), wherein $LG^1$ is a first leaving group and $LG^2$ is a second leaving group; in the presence of a reducing agent; in an organic solvent; to yield the corresponding compound of formula (X-E)

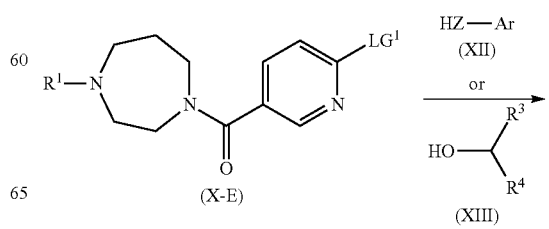

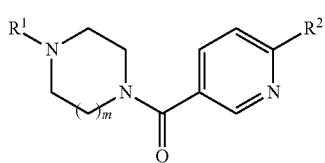

-continued

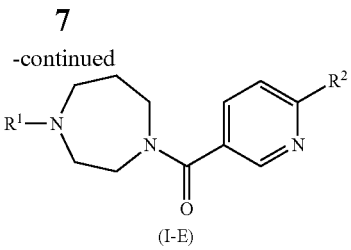

(I-E)

reacting the compound of formula (X-E) with a compound of formula (XII); in the presence of a first inorganic base; in an organic solvent; or reacting the compound of formula (X-E) with a compound of formula (XIII); in the presence of a second inorganic base; in an organic solvent;

to yield the corresponding compound of formula (I-E).

In an embodiment, the present invention is directed to processes for the preparation of compound (I-A)

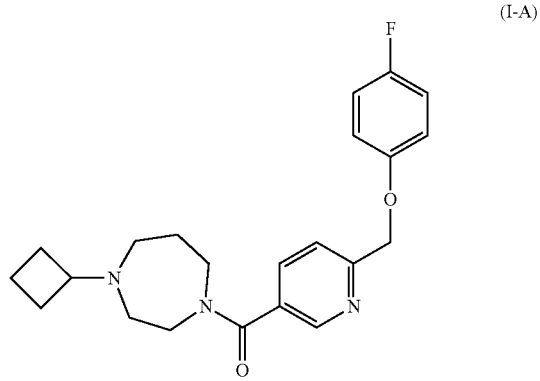 [SMILES: O=C(c1ccc(COc2ccc(F)cc2)nc1)N1CCCN(C2CCC2)CC1]

(I-A)

or a pharmaceutically acceptable salt, a pharmaceutically acceptable prodrug, or a pharmaceutically active metabolite thereof; also known as (4-cyclobutyl-[1,4]diazepan-1-yl)-[6-(4-fluoro-phenoxy)-pyridin-3-yl]-methanone; as described in more detail herein.

In another embodiment, the present invention is directed to a process for the preparation of compound (I-B)

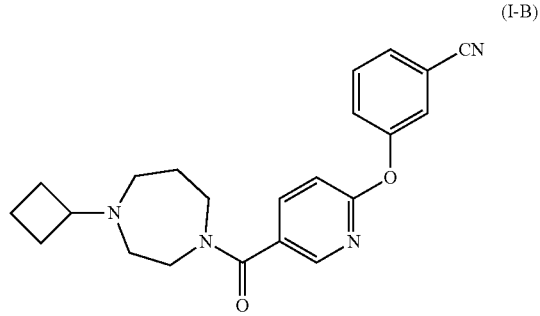 [SMILES: N#Cc1cccc(Oc2ccc(C(=O)N3CCCN(C4CCC4)CC3)cn2)c1]

(I-B)

or a pharmaceutically acceptable salt, a pharmaceutically acceptable prodrug, or a pharmaceutically active metabolite thereof; also known as 3-[5-(4-cyclobutyl-[1,4]diazepane-1-carbonyl)-pyridin-2-yloxy]-benzonitrile; as described in more detail herein.

In another embodiment, the present invention is directed to a process for the preparation of compound (I-C)

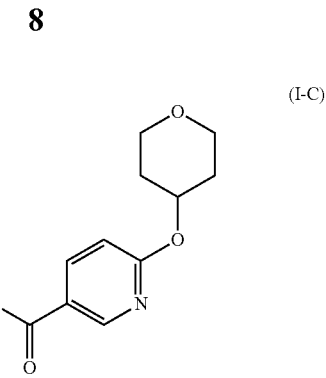

(I-C)

or a pharmaceutically acceptable salt, a pharmaceutically acceptable prodrug, or a pharmaceutically active metabolite thereof; also known as (4-cyclobutyl-[1,4]diazepan-1-yl)-[6-(tetrahydro-pyran-4-yloxy)-pyridin-3-yl]-methanone; as described in more detail herein.

The present invention is directed to processes for the preparation of compounds of formula (X)

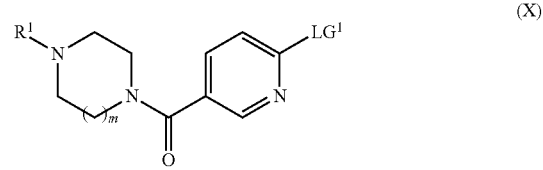

(X)

wherein $R^1$ is selected from the group consisting of $C_{1-4}$alkyl and $C_{3-10}$cycloalkyl;

m is an integer from 1 to 2;

$LG^1$ is a first leaving group;

or a pharmaceutically acceptable salt, thereof; comprising

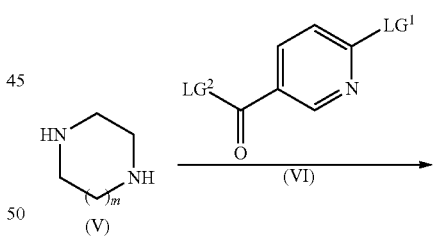

reacting a compound of formula (V) with a compound of formula (VI), wherein $LG^2$ is a second leaving group, in the presence of a base, in an organic solvent; to yield the corresponding compound of formula (VII);

(VII)

(X)

reacting the compound of formula (VII) with an aldehyde or ketone derivative of the desired $R^1$ substituent group; in the presence of a reducing agent; in an organic solvent; to yield the corresponding compound of formula (X).

The present invention is further directed to a process for the preparation of compounds of formula (X-E)

(X-E)

wherein
$R^1$ is selected from the group consisting of $C_{1-4}$alkyl and $C_{3-10}$cycloalkyl;
m is 2;
$LG^1$ is a first leaving group;
or a pharmaceutically acceptable salt, thereof; comprising (V-S) → (IX)

reacting a compound of formula (V-S) with an aldehyde or ketone derivative of the desired $R^1$ substituent group; neat or in an organic solvent; to yield the corresponding compound of formula (IX);

(IX) → (XI)

reacting the compound of formula (IX) with a reducing agent; neat, in water or an aqueous organic solvent; to yield the corresponding compound of formula (XI);

(XI) + (VI) →

(X-E)

reacting the compound of formula (XI) with a compound of formula (VI), wherein $LG^2$ is a second leaving group; in an organic solvent;

alternatively reacting the compound of formula (XI) with a compound of formula (VI), wherein $LG^1$ is a first leaving group and $LG^2$ is a second leaving group; in the presence of a base; in a mixture of water and an organic solvent;

to yield the corresponding compound of formula (X-E).

The present invention is further directed to a process for the preparation of compounds of formula (X-E)

(X-E)

wherein
$R^1$ is selected from the group consisting of $C_{1-4}$alkyl and $C_{3-10}$cycloalkyl;
m is 2;
$LG^1$ is a first leaving group;
or a pharmaceutically acceptable salt, thereof; comprising (V-S) → (IX)

reacting a compound of formula (V-S) with an aldehyde or ketone derivative of the desired $R^1$ substituent group; neat or in an organic solvent; to yield the corresponding compound of formula (IX);

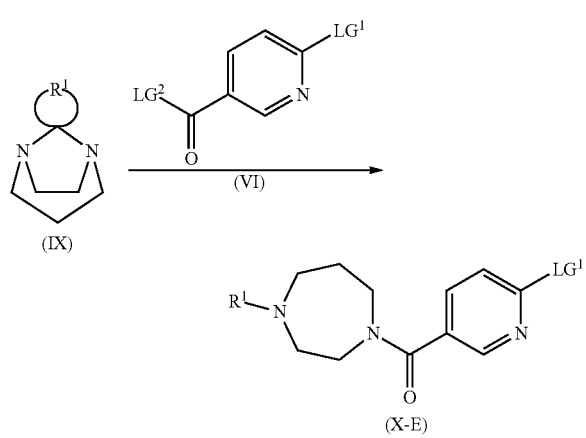

reacting the compound of formula (IX) with a compound of formula (VI), wherein LG² is a second leaving group; in the presence of a reducing agent; in an organic solvent; to yield the corresponding compound of formula (X-E).

In an embodiment, the present invention is directed to processes for the preparation of compounds of formula (X-S)

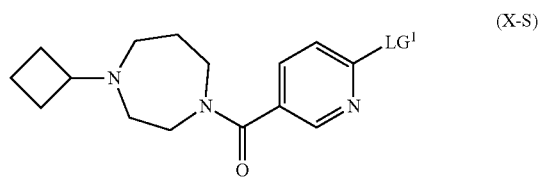

wherein LG¹ is a first leaving group; or pharmaceutically acceptable salt thereof; as described in more detail herein. The present invention is further directed to a process for the purification of the compound of formula (X-S), as described in more detail herein.

The present invention is further directed to two novel crystalline HCl salts of compound (I-B), as described in more detail hereinafter, and as referred to as FORM I and FORM II. The present invention is further directed to processes for the preparation of the crystalline HCl salts of compound (I-B).

The present invention is further directed to a novel crystalline HCl salt of compound (I-C), as described in more detail hereinafter. The present invention is further directed to a process for the preparation of the crystalline HCl salt of compound (I-C).

The present invention is further directed to a product prepared according to any of the processes described herein.

Illustrative of the invention is a pharmaceutical composition comprising a pharmaceutically acceptable carrier and any compound, crystalline salt or product as described herein. An illustration of the invention is a pharmaceutical composition made by mixing any compound, crystalline salt or product as described herein and a pharmaceutically acceptable carrier. Illustrating the invention is a process for making a pharmaceutical composition comprising mixing any compound, crystalline salt or product as described herein and a pharmaceutically acceptable carrier.

In another general aspect, the present invention is directed to methods for treating a subject suffering from or diagnosed with a disease, disorder, or medical condition mediated by histamine H₃ receptor activity, comprising administering to a subject in need of such treatment an effective amount of any compound, crystalline salt or product as described herein. In certain preferred embodiments of the present invention, the disease, disorder, or medical condition is selected from the group consisting of cognitive disorders, sleep disorders, psychiatric disorders, and other disorders.

In another aspect, the present invention is directed to the use of any compound, crystalline salt or product as described herein for the preparation of a medicament for the treatment of a disease, disorder, or medical condition mediated by histamine H₃ receptor activity, including (a) cognitive disorders, (b) sleep disorders, (c) psychiatric disorders, and other disorders.

BRIEF DESCRIPTION OF THE FIGURES

FIG. 3 illustrates a powder XRD spectrum for the crystalline HCl salt of compound (I-C).

DETAILED DESCRIPTION OF THE INVENTION

Figure 1:
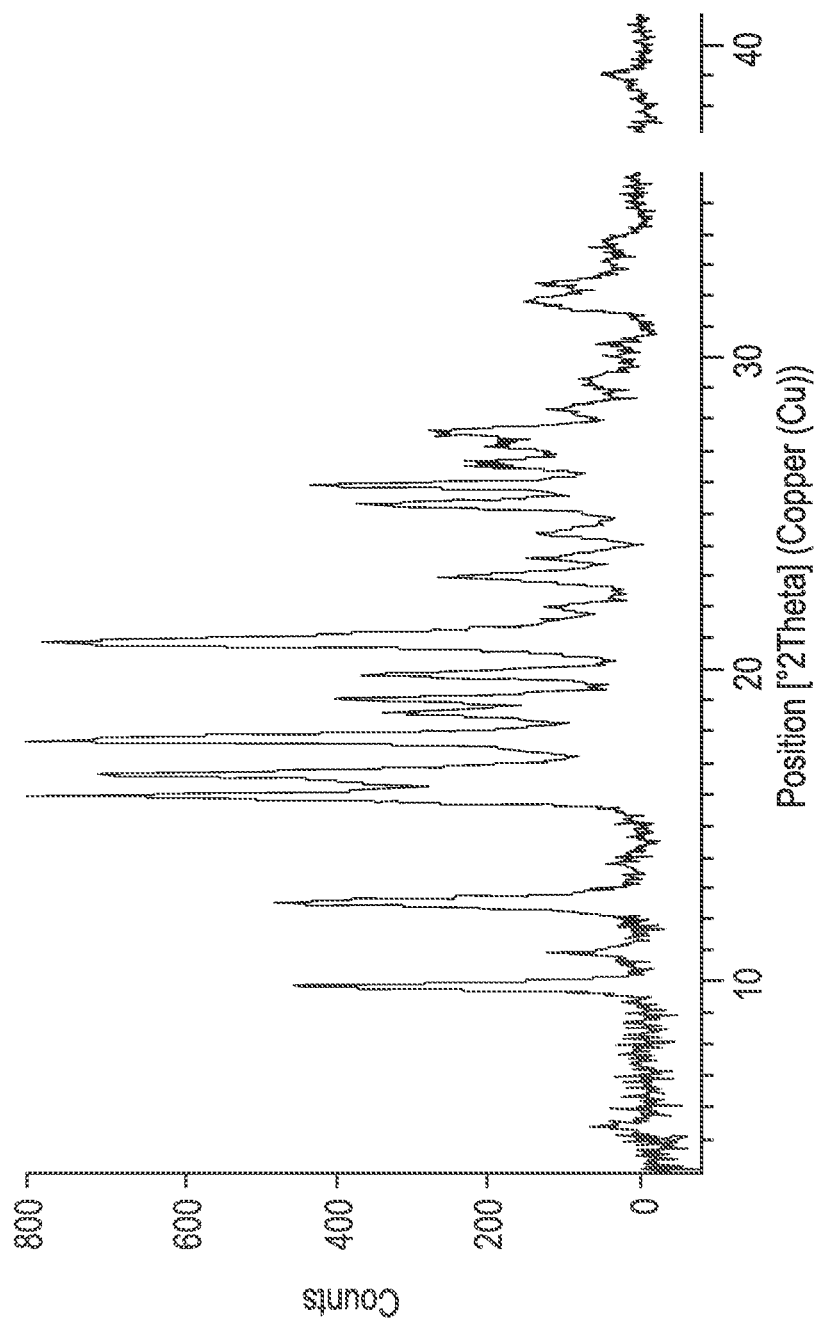
FIG. 1 illustrates a powder XRD spectrum for the crystalline HCl salt of compound (I-B), FORM I.

The present invention is directed to processes for the preparation of compounds of formula (I)

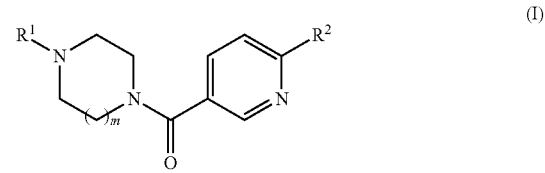

wherein $R^1$, m and $R^2$ are as herein defined; and pharmaceutically acceptable salts, pharmaceutically acceptable prodrugs, and pharmaceutically active metabolites thereof. The compounds of formula (I) are useful in the treatment of histamine H3 receptor modulated diseases, disorders and/or conditions, including but not limited to cognitive disorders, sleep disorders, psychiatric disorders and other disorders.

The present invention is directed to processes for the preparation of compounds of formula (I-E)

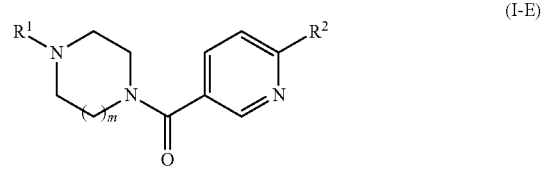

wherein m is 2 and wherein $R^1$, $R^2$ are as herein defined; and pharmaceutically acceptable salts, pharmaceutically acceptable prodrugs, and pharmaceutically active metabolites thereof. The compounds of formula (I-E) are useful in the treatment of histamine H3 receptor modulated diseases, disorders and/or conditions, including but not limited to cognitive disorders, sleep disorders, psychiatric disorders and other disorders.

The present invention is further directed to processes for the preparation of compounds of formula (X), including for example, the compound of formula (X-S), useful as intermediates in the synthesis of compounds of formula (I). In an example, the compound of formula (X-S) is useful as an intermediate in the synthesis of compounds (I-A), (I-B), (I-C) and pharmaceutically acceptable salts thereof. The present invention is further directed to process for the purification and isolation of a compound of formula (X-S), as described in more detail hereinafter.

The present invention is further directed to novel crystalline HCl salts of compound (I-B), more particularly FORM I and FORM II as described in more detail hereinafter. The present invention is further directed to a process for the preparation of the novel crystalline HCl salts of compound (I-B). The present invention is further directed to a novel crystalline HCl salt of compound (I-C). The present invention is further directed to a process for the preparation of the novel crystalline HCl salt of compound (I-C).

In preferred embodiments of the present invention, $R^1$ is methyl, ethyl, propyl, isopropyl, butyl, sec-butyl, or tert-butyl. In other preferred embodiments, $R^1$ is methyl or isopropyl. In still other preferred embodiments, $R^1$ is isopropyl, cyclopropyl, cyclobutyl, or cyclopentyl. In still other preferred embodiments, $R^1$ is cyclopropyl, cyclobutyl, cyclopentyl, or cyclohexyl. In still other preferred embodiments, $R^1$ is cyclopropyl or cyclobutyl.

In certain preferred embodiments, m is 1. In other preferred embodiments, m is 2.

In certain preferred embodiments, $R^2$ is —OCHR$^3$R$^4$. In other preferred embodiments, $R^2$ is —Z—Ar.

In certain preferred embodiments, $R^3$ is —H and $R^4$ is cyclopropyl, cyclocyclobutyl, or 3-methyl-oxetan-3-yl. In other embodiments, $R^3$ and $R^4$ are taken together with the carbon to which they are attached to form cyclobutyl, cyclopentyl, cyclohexyl, tetrahydrofuranyl, tetrahydropyranyl, oxepanyl, tetrahydrothiophenyl, tetrahydrothiopyranyl, pyrrolidinyl, thiepanyl, piperidinyl, or azepanyl, unsubstituted or substituted with methyl, ethyl, isopropyl, or acetyl.

In still other embodiments, —OCHR$^3$R$^4$ is selected from the group consisting of tetrahydro-furan-3-yloxy, 3-methyl-oxetan-3-ylmethoxy, cyclopentyloxy, cyclohexyloxy, tetrahydro-pyran-4-yloxy, tetrahydro-pyran-3-yloxy, cyclobutyloxy, oxepan-4-yloxy, oxepan-3-yloxy, cyclobutylmethoxy, cyclopropylmethoxy, tetrahydro-thiophen-3-yloxy, tetrahydro-thiopyran-4-yloxy, 1-methyl-pyrrolidin-3-yloxy, l-acetyl-pyrrolidin-3-yloxyl, thiepan-3-yloxy, thiepan-4-yloxy, 1-methyl-piperidin-4-yloxy, 1-acetyl-piperidin-4-yloxy, 1-isopropyl-azepan-4-yloxy, 1-acetyl-azepan-4-yloxy, 1-ethyl-azepan-3-yloxy, or 1-acetyl-azepan-3-yloxy. In still other embodiments, —OCHR$^3$R$^4$ is tetrahydro-furan-3-yloxy, 3-methyl-oxetan-3-ylmethoxy, cyclopentyloxy, cyclohexyloxy, and tetrahydro-pyran-4-yloxy. In still other preferred embodiments, —OCHR$^3$R$^4$ is tetrahydro-pyran-4-yloxy and m is 2.

In certain preferred embodiments, Z is O. In other preferred embodiments, Z is S.

In certain preferred embodiments, Ar is selected from the group consisting of a phenyl, pyrrolyl, furanyl, thiophenyl, imidazolyl, pyrazolyl, oxazolyl, isoxazolyl, thiazolyl, pyridyl, pyrimidinyl, and pyrazinyl group; wherein each Ar may be unsubstituted or substituted with one, two, or three $R^5$ substituents. In other preferred embodiments, Ar is a phenyl group unsubstituted or substituted with one, two, or three $R^5$ substituents. In still other preferred embodiments, Ar is a 4-halophenyl group. In further preferred embodiments, Ar is selected from the group consisting of phenyl, 3,4-dichlorophenyl, 4-methylsulfanylphenyl, 3-chlorophenyl, 3-fluorophenyl, 4-chloro-3-methylphenyl, 3-cyanophenyl, 4-chlorophenyl, 4-fluorophenyl, 3,4-difluorophenyl, 2-fluorophenyl, 3-chlorophenyl, 2,4-difluorophenyl, 3,5-dichlorophenyl, 2,5-difluorophenyl, 3,5-difluorophenyl, 3-methyl-4-methylsulfanylphenyl, and 3-pyridyl.

In certain embodiments of the present invention, the compound of formula (I) is selected from the group consisting of (4-cyclobutyl-[1,4]diazepan-1-yl)-[6-(4-fluoro-phenoxy)-pyridin-3-yl]-methanone; 3-[5-(4-cyclobutyl-[1,4]diazepane-1-carbonyl)-pyridin-2-yloxy]-benzonitrle; and (4-cyclobutyl-[1,4]diazepan-1-yl)-[6-(tetrahydro-pyran-4-yloxy)-pyridin-3-yl]-methanone; and pharmaceutically acceptable salts, prodrugs and active metabolites thereof.

In certain preferred embodiments, the compound of formula (I) is selected from the group consisting of compound (I-A), compound (I-B), compound (I-C) and pharmaceutically acceptable salts thereof.

In certain preferred embodiments, the compound of formula (I) is one or more selected from the group consisting of

| ID No. | Chemical Name |
| --- | --- |
| 1 | [6-(3,4-Dichloro-phenoxy)-pyridin-3-yl]-(4-isopropyl-piperazin-1-yl)-methanone; |
| 2 | (4-Isopropyl-piperazin-1-yl)-[6-(pyridin-3-yloxy)-pyridin-3-yl]-methanone; |
| 3 | (4-Isopropyl-piperazin-1-yl)-[6-(4-methylsulfanyl-phenoxy)-pyridin-3-yl]-methanone; |
| 4 | [6-(3-Chloro-phenoxy)-pyridin-3-yl]-(4-isopropyl-piperazin-1-yl)-methanone; |
| 5 | (4-Isopropyl-piperazin-1-yl)-(6-phenoxy-pyridin-3-yl)-methanone; |
| 6 | [6-(4-Chloro-3-methyl-phenoxy)-pyridin-3-yl]-(4-isopropyl-piperazin-1-yl)-methanone; |
| 7 | 3-[5-(4-Isopropyl-piperazine-1-carbonyl)-pyridin-2-yloxy]-benzonitrile; |
| 8 | [6-(4-Chloro-phenoxy)-pyridin-3-yl]-(4-isopropyl-piperazin-1-yl)-methanone; |
| 9 | (4-Cyclopropyl-[1,4]diazepan-1-yl)-[6-(3,4-dichloro-phenoxy)-pyridin-3-yl]-methanone; |
| 10 | [6-(4-Chloro-phenoxy)-pyridin-3-yl]-(4-cyclopropyl-[1,4]diazepan-1-yl)-methanone; |
| 11 | 3-[5-(4-Cyclopropyl-[1,4]diazepane-1-carbonyl)-pyridin-2-yloxy]-benzonitrile; |
| 12 | [6-(4-Chloro-3-methyl-phenoxy)-pyridin-3-yl]-(4-cyclopropyl-[1,4]diazepan-1-yl)-methanone; |
| 13 | (4-Cyclopropyl-[1,4]diazepan-1-yl)-(6-phenoxy-pyridin-3-yl)-methanone; |

-continued

| ID No. | Chemical Name |
|---|---|
| 14 | (4-Cyclobutyl-[1,4]diazepan-1-yl)-[6-(3,4-dichloro-phenoxy)-pyridin-3-yl]-methanone; |
| 15 | [6-(3,4-Dichloro-phenoxy)-pyridin-3-yl]-(4-isopropyl-[1,4]diazepan-1-yl)-methanone; |
| 16 | [6-(4-Chloro-3-methyl-phenoxy)-pyridin-3-yl]-(4-cyclobutyl-[1,4]diazepan-1-yl)-methanone; |
| 17 | [6-(4-Chloro-3-methyl-phenoxy)-pyridin-3-yl]-(4-isopropyl-[1,4]diazepan-1-yl)-methanone; |
| 18 | (4-Cyclopropyl-[1,4]diazepan-1-yl)-[6-(4-fluoro-phenoxy)-pyridin-3-yl]-methanone; |
| 19 | (4-Cyclobutyl-[1,4]diazepan-1-yl)-[6-(4-fluoro-phenoxy)-pyridin-3-yl]-methanone; |
| 20 | 3-[5-(4-Cyclobutyl-[1,4]diazepane-1-carbonyl)-pyridin-2-yloxy]-benzonitrile; |
| 21 | (4-Cyclobutyl-[1,4]diazepan-1-yl)-(6-phenoxy-pyridin-3-yl)-methanone; |
| 22 | (4-Cyclopropyl-piperazin-1-yl)-[6-(4-fluoro-phenoxy)-pyridin-3-yl]-methanone; |
| 23 | [6-(3-Chloro-phenoxy)-pyridin-3-yl]-(4-cyclopropyl-[1,4]diazepan-1-yl)-methanone; |
| 24 | [6-(3-Chloro-phenoxy)-pyridin-3-yl]-(4-cyclobutyl-[1,4]diazepan-1-yl)-methanone; |
| 25 | [6-(4-Chloro-phenoxy)-pyridin-3-yl]-(4-cyclobutyl-[1,4]diazepan-1-yl)-methanone; |
| 26 | (4-Cyclobutyl-[1,4]diazepan-1-yl)-[6-(3,4-difluoro-phenoxy)-pyridin-3-yl]-methanone; |
| 27 | (4-Cyclopropyl-[1,4]diazepan-1-yl)-[6-(3,4-difluoro-phenoxy)-pyridin-3-yl]-methanone; |
| 28 | [6-(3,4-Difluoro-phenoxy)-pyridin-3-yl]-(4-isopropyl-piperazin-1-yl)-methanone; |
| 29 | (4-Cyclobutyl-[1,4]diazepan-1-yl)-[6-(2-fluoro-phenoxy)-pyridin-3-yl]-methanone; |
| 30 | (4-Cyclobutyl-[1,4]diazepan-1-yl)-[6-(2,4-difluoro-phenoxy)-pyridin-3-yl]-methanone; |
| 31 | (4-Cyclopropyl-[1,4]diazepan-1-yl)-[6-(2-fluoro-phenoxy)-pyridin-3-yl]-methanone; |
| 32 | (4-Cyclopropyl-[1,4]diazepan-1-yl)-[6-(2,4-difluoro-phenoxy)-pyridin-3-yl]-methanone; |
| 33 | (4-Cyclobutyl-[1,4]diazepan-1-yl)-[6-(3,5-dichloro-phenoxy)-pyridin-3-yl]-methanone; |
| 34 | (4-Cyclopropyl-[1,4]diazepan-1-yl)-[6-(2,5-difluoro-phenoxy)-pyridin-3-yl]-methanone; |
| 35 | (4-Cyclopropyl-[1,4]diazepan-1-yl)-[6-(3,5-dichloro-phenoxy)-pyridin-3-yl]-methanone; |
| 36 | (4-Cyclobutyl-[1,4]diazepan-1-yl)-[6-(3,5-difluoro-phenoxy)-pyridin-3-yl]-methanone; |
| 37 | (4-Cyclopropyl-[1,4]diazepan-1-yl)-[6-(3-fluoro-phenoxy)-pyridin-3-yl]-methanone; |
| 38 | [6-(3-Fluoro-phenoxy)-pyridin-3-yl]-(4-isopropyl-[1,4]diazepan-1-yl)-methanone; |
| 39 | (4-Cyclobutyl-[1,4]diazepan-1-yl)-[6-(3-fluoro-phenoxy)-pyridin-3-yl]-methanone; |
| 40 | (4-Cyclobutyl-[1,4]diazepan-1-yl)-[6-(3-methyl-4-methylsulfanyl-phenoxy)-pyridin-3-yl]-methanone; |
| 41 | (4-Cyclopropyl-[1,4]diazepan-1-yl)-[6-(3-methyl-4-methylsulfanyl-phenoxy)-pyridin-3-yl]-methanone; |
| 42 | (4-Isopropyl-[1,4]diazepan-1-yl)-[6-(3-methyl-4-methylsulfanyl-phenoxy)-pyridin-3-yl]-methanone; |
| 65 | (4-Cyclopentyl-[1,4]diazepan-1-yl)-(6-phenoxy-pyridin-3-yl)-methanone; |
| 66 | (4-Cyclopentyl-[1,4]diazepan-1-yl)-[6-(3,4-dichloro-phenoxy)-pyridin-3-yl]-methanone; |
| 67 | (4-Cyclopentyl-[1,4]diazepan-1-yl)-[6-(4-fluoro-phenoxy)-pyridin-3-yl]-methanone; |
| 73 | [6-(2-Chloro-phenoxy)-pyridin-3-yl]-(4-cyclobutyl-[1,4]diazepan-1-yl)-methanone; |
| 74 | (4-Cyclopentyl-piperazin-1-yl)-[6-(4-fluoro-phenoxy)-pyridin-3-yl]-methanone; |
| 75 | [6-(2-Chloro-phenoxy)-pyridin-3-yl]-(4-isopropyl-piperazin-1-yl)-methanone; |
| 76 | [6-(2-Chloro-phenoxy)-pyridin-3-yl]-(4-cyclopentyl-piperazin-1-yl)-methanone; |
| 77 | [6-(4-Chloro-phenoxy)-pyridin-3-yl]-(4-cyclopentyl-piperazin-1-yl)-methanone; |
| 78 | (4-Cyclopentyl-piperazin-1-yl)-[6-(2-fluoro-phenoxy)-pyridin-3-yl]-methanone; |
| 79 | (4-Cyclobutyl-piperazin-1-yl)-[6-(4-fluoro-phenoxy)-pyridin-3-yl]-methanone; |

| ID No. | Chemical Name |
|---|---|
| 80 | [6-(4-Fluoro-phenoxy)-pyridin-3-yl]-(4-methyl-[1,4]diazepan-1-yl)-methanone; |
| 83 | (4-Cyclobutyl-[1,4]diazepan-1-yl)-[6-(4-fluoro-phenylsulfanyl)-pyridin-3-yl]-methanone; |
| 85 | [6-(4-Chloro-phenylsulfanyl)-pyridin-3-yl]-(4-cyclobutyl-[1,4]diazepan-1-yl)-methanone; |
| 86 | (4-Cyclobutyl-[1,4]diazepan-1-yl)-(6-phenylsulfanyl-pyridin-3-yl)-methanone; |
| 87 | (4-Cyclopentyl-piperazin-1-yl)-[6-(3-methyl-4-methylsulfanyl-phenoxy)-pyridin-3-yl]-methanone; |
| 88 | (4-Isopropyl-piperazin-1-yl)-[6-(3-methyl-4-methylsulfanyl-phenoxy)-pyridin-3-yl]-methanone; |
| 89 | [6-(4-Fluoro-phenoxy)-pyridin-3-yl]-(4-isopropyl-piperazin-1-yl)-methanone; |
| 90 | (4-Ethyl-[1,4]diazepan-1-yl)-[6-(4-fluoro-phenoxy)-pyridin-3-yl]-methanone; |
| 92 | [6-(4-Fluoro-phenoxy)-pyridin-3-yl]-(4-methyl-[1,4]diazepan-1-yl)-methanone; |
| 93 | [6-(4-Fluoro-phenoxy)-pyridin-3-yl]-(4-isobutyl-piperazin-1-yl)-methanone; |
| 95 | (4-Cyclobutyl-[1,4]diazepan-1-yl)-(6-phenylsulfanyl-pyridin-3-yl)-methanone; |
| 96 | [6-(4-Chloro-phenylsulfanyl)-pyridin-3-yl]-(4-cyclobutyl-[1,4]diazepan-1-yl)-methanone; |
| 97 | (4-Cyclobutyl-[1,4]diazepan-1-yl)-[6-(4-fluoro-phenylsulfanyl)-pyridin-3-yl]-methanone; |
| 98 | (4-Ethyl-[1,4]diazepan-1-yl)-[6-(4-fluoro-phenoxy)-pyridin-3-yl]-methanone; |
| 99 | [6-(4-Fluoro-phenoxy)-pyridin-3-yl]-(4-isopropyl-piperazin-1-yl)-methanone; |
| 100 | (4-Cyclopentyl-piperazin-1-yl)-[6-(3-methyl-4-methylsulfanyl-phenoxy)-pyridin-3-yl]-methanone; |
| 101 | (4-Isopropyl-piperazin-1-yl)-[6-(3-methyl-4-methylsulfanyl-phenoxy)-pyridin-3-yl]-methanone; |
| 102 | (4-Cyclobutyl-[1,4]diazepan-1-yl)-(6-o-tolyloxy-pyridin-3-yl)-methanone; |
| 103 | (4-Cyclobutyl-[1,4]diazepan-1-yl)-(6-m-tolyloxy-pyridin-3-yl)-methanone; |
| 104 | (4-Cyclobutyl-[1,4]diazepan-1-yl)-(6-p-tolyloxy-pyridin-3-yl)-methanone; and |
| 105 | (4-Cyclobutyl-[1,4]diazepan-1-yl)-[6-(4-methylsulfanyl-phenoxy)-pyridin-3-yl]-methanone; | and pharmaceutically acceptable salts thereof.

In certain preferred embodiments, the compound of formula (I) is one or more selected from the group consisting of

| ID No. | CHEMICAL NAME |
|---|---|
| 1 | (4-Isopropyl-piperazin-1-yl)-[6-(tetrahydro-furan-3-yloxy)-pyridin-3-yl]-methanone; |
| 2 | (4-Isopropyl-[1,4]diazepan-1-yl)-[6-(tetrahydro-furan-3-yloxy)-pyridin-3-yl]-methanone; |
| 3 | (4-Cyclopropyl-[1,4]diazepan-1-yl)-[6-(tetrahydro-furan-3-yloxy)-pyridin-3-yl]-methanone; |
| 4 | (4-Cyclobutyl-[1,4]diazepan-1-yl)-[6-(tetrahydro-furan-3-yloxy)-pyridin-3-yl]-methanone; |
| 5 | (4-Isopropyl-piperazin-1-yl)-[6-(3-methyl-oxetan-3-ylmethoxy)-pyridin-3-yl]-methanone; |
| 6 | (4-Isopropyl-[1,4]diazepan-1-yl)-[6-(3-methyl-oxetan-3-ylmethoxy)-pyridin-3-yl]-methanone; |
| 7 | (4-Cyclobutyl-[1,4]diazepan-1-yl)-(6-cyclopentyloxy-pyridin-3-yl)-methanone; |
| 8 | (4-Cyclobutyl-[1,4]diazepan-1-yl)-(6-cyclohexyloxy-pyridin-3-yl)-methanone; |
| 9 | (4-Cyclobutyl-[1,4]diazepan-1-yl)-[6-(tetrahydro-pyran-4-yloxy)-pyridin-3-yl]-methanone; |
| 13 | (4-Isopropyl-[1,4]diazepan-1-yl)-[6-(tetrahydro-pyran-4-yloxy)-pyridin-3-yl]-methanone; |
| 14 | (4-Cyclopropyl-[1,4]diazepan-1-yl)-[6-(tetrahydro-pyran-4-yloxy)-pyridin-3-yl]-methanone; |
| 15 | (4-Cyclopentyl-[1,4]diazepan-1-yl)-[6-(tetrahydro-pyran-4-yloxy)-pyridin-3-yl]-methanone; |
| 16 | (4-Isopropyl-piperazin-1-yl)-[6-(tetrahydro-pyran-4-yloxy)-pyridin-3-yl]-methanone; |

| ID No. | CHEMICAL NAME |
|---|---|
| 17 | (4-Cyclopropyl-piperazin-1-yl)-[6-(tetrahydro-pyran-4-yloxy)-pyridin-3-yl]-methanone; |
| 18 | (4-Cyclobutyl-piperazin-1-yl)-[6-(tetrahydro-pyran-4-yloxy)-pyridin-3-yl]-methanone; |
| 19 | (4-Cyclopentyl-piperazin-1-yl)-[6-(tetrahydro-pyran-4-yloxy)-pyridin-3-yl]-methanone; |
| 22 | (6-Cyclobutoxy-pyridin-3-yl)-(4-cyclobutyl-[1,4]diazepan-1-yl)-methanone; |
| 23 | (4-Cyclobutyl-[1,4]diazepan-1-yl)-[6-(oxepan-4-yloxy)-pyridin-3-yl]-methanone; |
| 24 | (4-Cyclobutyl-[1,4]diazepan-1-yl)-[6-(oxepan-3-yloxy)-pyridin-3-yl]-methanone; |
| 25 | (4-Cyclobutyl-[1,4]diazepan-1-yl)-(6-cyclobutylmethoxy-pyridin-3-yl)-methanone; |
| 26 | (4-Cyclobutyl-[1,4]diazepan-1-yl)-(6-cyclopropylmethoxy-pyridin-3-yl)-methanone; |
| 27 | (4-Cyclobutyl-[1,4]diazepan-1-yl)-[6-(tetrahydro-thiophen-3-yloxy)-pyridin-3-yl]-methanone; |
| 28 | (4-Cyclobutyl-[1,4]diazepan-1-yl)-[6-(tetrahydro-thiopyran-4-yloxy)-pyridin-3-yl]-methanone; |
| 29 | (4-Cyclobutyl-[1,4]diazepan-1-yl)-[6-(1-methyl-pyrrolidin-3-yloxy)-pyridin-3-yl]-methanone; |
| 30 | 1-{3-[5-(4-Cyclobutyl-[1,4]diazepane-1-carbonyl)-pyridin-2-yloxy]-pyrrolidin-1-yl}-ethanone; |
| 31 | (4-Cyclobutyl-[1,4]diazepan-1-yl)-[6-(thiepan-3-yloxy)-pyridin-3-yl]-methanone; |
| 32 | (4-Cyclobutyl-[1,4]diazepan-1-yl)-[6-(thiepan-4-yloxy)-pyridin-3-yl]-methanone; |
| 33 | (4-Cyclobutyl-[1,4]diazepan-1-yl)-[6-(1-methyl-piperidin-4-yloxy)-pyridin-3-yl]-methanone; |
| 34 | 1-{4-[5-(4-Cyclobutyl-[1,4]diazepane-1-carbonyl)-pyridin-2-yloxy]-piperidin-1-yl}-ethanone; |
| 35 | (4-Cyclobutyl-[1,4]diazepan-1-yl)-[6-(1-isopropyl-azepan-4-yloxy)-pyridin-3-yl]-methanone; |
| 36 | 1-{4-[5-(4-Cyclobutyl-[1,4]diazepane-1-carbonyl)-pyridin-2-yloxy]-azepan-1-yl}-ethanone; |
| 37 | (4-Cyclobutyl-[1,4]diazepan-1-yl)-[6-(1-ethyl-azepan-3-yloxy)-pyridin-3-yl]-methanone; and |
| 38 | 1-{3-[5-(4-Cyclobutyl-[1,4]diazepane-1-carbonyl)-pyridin-2-yloxy]-azepan-1-yl}-ethanone; and |
| 39 | (4-Cyclopropyl-piperazin-1-yl)-[6-(tetrahydro-pyran-3-yloxy)-pyridin-3-yl]-methanone; |

The term "halogen" represents chlorine, fluorine, bromine or iodine. The term "halo" represents chloro, fluoro, bromo or iodo.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated monocyclic carbocycle having from 3 to 10 ring atoms per carbocycle. Illustrative examples of cycloalkyl groups include cyclopropyl, cyclobutyl, cyclopentyl, cyclohexyl, cycloheptyl, cyclooctyl, cyclononyl and cyclodecyl.

The term "heteroaryl" refers to a monocyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include furyl, pyrrolyl, thiophenyl, imidazolyl, pyrazolyl, oxazolyl, isoxazolyl, thiazolyl, isothiazolyl, tetrazolyl, pyridyl, pyrimidinyl, pyrazinyl, pyridazinyl and triazinyl.

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

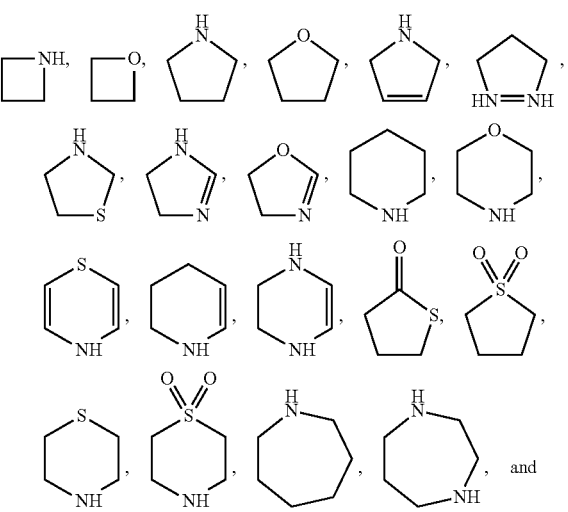

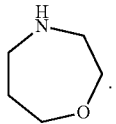

Those skilled in the art will recognize that the species of cycloalkyl, heterocycloalkyl, and heteroaryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^6Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Abbreviations used in the specification, particularly the Schemes and Examples, are as follows:
DCE=1,1-Dichloroethane
DMA=N,N-Dimethylacetamide
DMF=N,N-Dimethylformamide
DMSO=Dimethylsulfoxide
HOAc=Acetic Acid
IPA=Isopropyl Alcohol (Isopropanol)
iPrOAc=Isopropyl Acetate
KO-t-Bu=Potassium t-Butoxide
LiOEt=Lithium Ethoxide
2-Me-THF=2-Methyl-tetrahydrofuran
MTBE=Methyl t-butyl Ether
NaOAc=Sodium Acetate
NaO-t-Bu=Sodium t-Butoxide
NMP=N-methyl-2-pyrrolidinone
TFA=Trifluoroacetic Acid
THF=Tetrahydrofuran As used herein, unless otherwise noted, the term "isolated form" shall mean that the compound is present in a form which is separate from any solid mixture with another compound(s), solvent system or biological environment. In an embodiment, the present invention is directed to a process for the preparation of a compound of formula (I) as an isolated form. In another embodiment, the present invention is directed to a process for the preparation of compound (I-A) as an isolated form. In another embodiment, the present invention is directed to a process for the preparation of compound (I-B) as an isolated form. In another embodiment, the present invention is directed to a process for the preparation of compound (I-C) as an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a process for the preparation of a compound of formula (I) as a substantially pure form. In another embodiment, the present invention is directed to a process for the preparation of compound (I-A) as a substantially pure form. In another embodiment, the present invention is directed to a process for the preparation of compound (I-B) as a substantially pure form. In another embodiment, the present invention is directed to a process for the preparation of compound (I-C) as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the present invention is directed to a process for the preparation of a compound of formula (I) in a form which is substantially free of corresponding salt forms. In another embodiment, the present invention is directed to a process for the preparation of compound (I-A) in a form which is substantially free of corresponding salt forms. In another embodiment, the present invention is directed to a process for the preparation of compound (I-B) in a form which is substantially free of corresponding salt forms. In another embodiment, the present invention is directed to a process for the preparation of compound (I-C) in a form which is substantially free of corresponding salt forms.

A "pharmaceutically acceptable salt" is intended to mean a salt of a free acid or base of a compound represented by Formula (I) that is non-toxic, biologically tolerable, or otherwise biologically suitable for administration to the subject. See, generally, BERGE, S. M., et al., "Pharmaceutical Salts", *J. Pharm. Sci.,* 1977, pp 1-19, vol. 66; and *Handbook of Pharmaceutical Salts, Properties, Selection, and Use*. Stahl and Wermuth (Editors), Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in *Design of Prodrugs*, H. Bundgaard (Editor), Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$ alkyl amines and secondary di($C_{1-6}$alkyl)amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in FLEISHER, D., et al., "Improved oral drug delivery: solubility limitations overcome by the use of prodrugs", Adv. Drug Delivery Rev., 1996, pp 115-130, vol. 19. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in ROBINSON, R. P., et al., "Discovery of the hemifumarate and (alpha-L-alanyloxy)methyl ether as prodrugs of an antirheumatic oxindole: prodrugs for the enolic OH group", J. Med. Chem., 1996, pp 10-18, vol. 39. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., BERTOLINI, et al., "A new rational hypothesis for the pharmacophore of the active metabolite of leflunomide, a potent immunosuppressive drug", J. Med. Chem., 1997, pp 2011-2016, vol. 40; SHAN, et al., "Prodrug strategies based on intramolecular cyclization reactions", J. Pharm. Sci., 1997, pp 765-767, Vol. 86, Issue 7; BAGSHAWE, K. D., "Antibody-directed Enzyme Prodrug Therapy: A Review", Drug Dev. Res., 1995, pp 220-230, Vol. 34; BODOR, N., "Novel Approaches to the Design of Safer Drugs: Soft Drugs and Site-Specific Chemical Delivery Systems", Adv. Drug Res., 1984, pp 224-331, Vol. 13; Bundgaard, H, Design of Prodrugs, Elsevier Press, 1985; and Larsen, Design and Application of Prodrugs, Drug Design and Development, Krogsgaard-Larsen, et al. (Editors), Harwood Academic Publishers, 1991.

The compounds of formula (I) and their pharmaceutically acceptable salts, pharmaceutically acceptable prodrugs, and pharmaceutically active metabolites of the present invention are useful as modulators of the histamine $H_3$ receptor in the methods of the invention. As such modulators, the compounds may act as antagonists, agonists, or inverse agonists. "Modulators" include both inhibitors and activators, where "inhibitors" refer to compounds that decrease, prevent, inactivate, desensitize or down-regulate histamine $H_3$ receptor expression or activity, and "activators" are compounds that increase, activate, facilitate, sensitize, or up-regulate histamine $H_3$ receptor expression or activity.

The term "treat" or "treating" as used herein is intended to refer to administration of an active agent or composition of the invention to a subject for the purpose of effecting a therapeutic or prophylactic benefit through modulation of histamine $H_3$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by histamine $H_3$ receptor activity, such as: cognitive disorders, sleep disorders, psychiatric disorders, and other disorders. Symptoms or disease states are intended to be included within the scope of "medical conditions, disorders, or diseases."

"Cognitive disorders" include, for example, dementia, Alzheimer's disease (PANULA, P. et al., "Significant Changes in the Human Brain Histaminergic System in Alzheimer's Disease", Soc. Neurosci. Abstr., 1995, pp 1977, vol. 21), cognitive dysfunction, mild cognitive impairment (pre-dementia), attention deficit hyperactivity disorders (ADHD), attention-deficit disorders, and learning and memory disorders (BARNES, J. C. et al., "The Selective Histamine H3 Receptor Antagonist Thioperamide Improves Cognition and Enhances Hippocampal Acetylcholine Release in vivo", Soc. Neurosci. Abstr., 1993, pp 1813, vol. 19). Learning and memory disorders include, for example, learning impairment, memory impairment, age-related cognitive decline, and memory loss. $H_3$ antagonists have been shown to improve memory in a variety of memory tests, including the elevated plus maze in mice (MIYAZAKI, S. et al., "Effects of thioperamide, a histamine $H_3$-receptor antagonist, on a scopolamine-induced learning deficit using an elevated plus-maze test in mice", Life Sci., 1995, pp 2137-2144, vol. 57, issue 23), a two-trial place recognition task (ORSETTI, M. et al., "Histamine H"3-receptor antagonism improves memory retention and reverses the cognitive deficit induced by scopolamine in a two-trial place recognition task", Behav. Brain Res., 2001, pp 235-242, vol 124, issue 2), the passive avoidance test in mice (MIYAZAKI, S. et al., "Effects of thioperamide on the cholinergic system and the step-through passive avoidance test in mice", Meth. Find. Exp. Clin. Pharmacol., 1995, pp 653-658, vol. 17, issue 10) and the radial maze in rats (CHEN, Z., "Effect of histamine H3-receptor antagonist clobenpropit on spatial memory of radial maze performance in rats", Acta Pharmacol. Sinica., 2000, pp 905-910, vol. 21, issue 10). Also, in the spontaneously hypertensive rat, an animal model for the learning impairments in attention-deficit disorders, $H_3$ antagonists were shown to improve memory (FOX, G. B. et al., "Effects of histamine H"3 receptor ligands GT-2331 and ciproxifan in a repeated acquisition avoidance response in the spontaneously hypertensive rat pup", *Behav. Brain Res.*, 2002, pp 151-161, vol. 131, issue 1-2).

"Sleep disorders" include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag (phase delay), and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

"Psychiatric disorders" include, for example, schizophrenia (SCHLICKER, E. et al., "The moderate affinity of clozapine at $H_3$ receptors is not shared by its two major metabolites and by structurally related and unrelated atypical neuroleptics", *Naunvn-Schmiedeberq's Arch. of Pharmacol.*, 1996, pp 290-294, vol. 353, issue 3), including cognitive deficits and negative symptoms associated with schizophrenia, bipolar disorders, manic disorders, depression (LAMBERTI, C. et al., "Antidepressant-like effects of endogenous histamine and of two histamine H1 receptor agonists in the mouse forced swim test", *Br. J. Pharmacol.*, 1998, pp 1331-1336, vol. 123, issue 7; PEREZ-GARCIA, C. et al., "Effects of Histamine H3 Receptor in Experimental Models of Anxiety and Depression", *Psychopharmacology,* 1999, pp 215-220, vol. 142, issue 2) (Also see: STARK, H. et al., "Developments of histamine $H_3$-receptor antagonist", *Drugs Future,* 1996, pp 507-520, Vol. 21, issue 5; and LEURS, R. et al., "The medicinal chemistry and therapeutic potentials of ligands of the histamine $H_3$ receptor", *Prog. Drug Res.,* 1995, pp 107-165, vol. 45 and references cited therein.), including bipolar depression, obsessive-compulsive disorder, and post-traumatic stress disorder.

"Other disorders" include, for example, motion sickness, vertigo (e.g. vertigo or benign postural vertigo), tinitus, epilepsy (YOKOYAMA, H. et al., "Effect of thioperamide, a histamine H3 receptor antagonist, on electrically induced convulsions in mice", *Eur. J. Pharmacol.,* 1993, pp 129-133, vol. 234), migraine, neurogenic inflammation, neuropathic pain, Down Syndrome, seizures, eating disorders (MACHIDORI, H. et al., "Zucker obese rats: defect in brain histamine control of feeding", *Brain Res.,* 1992, pp 180-186, vol. 590), obesity, substance abuse disorders, movement disorders (e.g. restless legs syndrome), and eye-related disorders (e.g. macular degeneration and retinitis pigmentosis).

Particularly, as modulators of the histamine $H_3$ receptor, the compounds prepared according to the processes of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In treatment methods according to the invention, an effective amount of at least one compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.1 to about 200 mg of compound per kg of subject's body weight per day, or any range therein, preferably about 0.01 to about 10 mg/kg/day, or about 0.01 to about 1.0 mg/kg/day, or any range therein, in single or divided dosage units (e.g., BID, TID, QID). For a 70-kg human, an illustrative range for a suitable dosage amount is from about 0.1 to about 100 mg/day, or any range therein, preferably from about 0.5 to about 50.0 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, bromo, chloro, fluoro, iodo, mesylate, tosylate, and the like. In a preferred example, the leaving group is bromo, chloro or iodo, more preferably, chloro.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, J. F. W. McOmie (Editor), Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α-obs]/[α-max])×100.

The present invention is directed to processes for the preparation of compounds of formula (X), useful as intermediates in the synthesis of the compounds of formula (I), as outlined in more detail in Schemes 1 through 4, which follow herein. The present invention is further directed to processes for the preparation of compounds of formula (I) from suitably substituted compounds of formula (X), as outlined in more detail in Schemes 5 through 7, which follow herein.

The present invention is directed to a process for the preparation of compounds of formula (X) as outlined in more detail in Scheme 1, below.

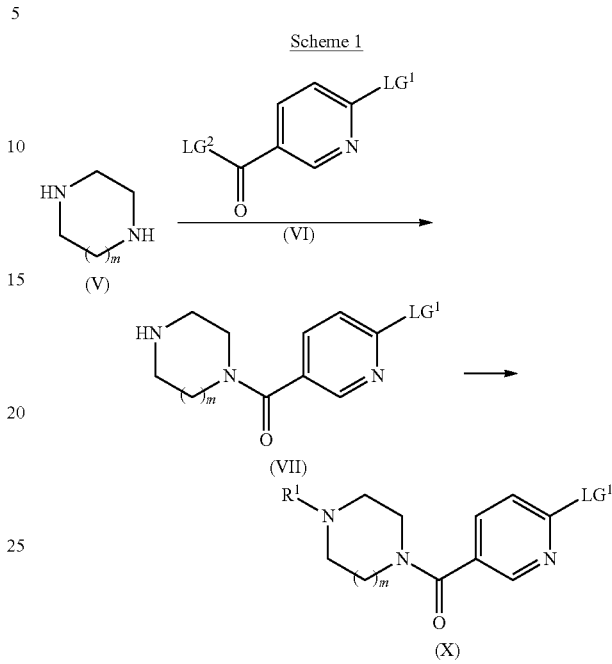

Accordingly, a suitably substituted compound of formula (V), a known compound or compound prepared by known methods is reacted with a suitably substituted compound of formula (VI), wherein $LG^1$ is a suitably selected first leaving group such as chloro, bromo, fluoro, and the like, preferably chloro, and wherein $LG^2$ is a second leaving group such $OC_{1-4}$alkyl, —O-phenyl, —O-benzyl, chloro, dimethylamino, diethylamino, and the like, preferably —O-methyl or —O— ethyl; a known compound or compound prepared by known methods; wherein the compound of formula (V) is present in an amount in the range of from about 1.0 to about 5.0 molar equivalents (relative to moles of the compound of formula (VI), more preferably in an amount in the range of from about 2.0 to about 3.0 molar equivalents, more preferably about 2.5 molar equivalents;

in the presence of a suitably selected base such as an alkyl lithium, such as n-hexyl lithium, n-butyl lithium and the like, or in the presence of a suitably selected base such as a lithium alkoxide or sodium alkoxide such as lithium ethoxide, lithium methoxide, sodium methoxide, and the like, or in the presence of a suitably selected base such as isopropyl magnesium chloride, and the like; preferably the base is an alkyl lithium, more preferably, the base is n-hexyl lithium; and when the base is an alkyl lithium, the base is preferably present in an amount in the range of from about 0.1 to about 3.0 molar equivalents (relative to the moles of the compound of formula (VI), more preferably in an amount in the range of form about 0.1 to about 1.0 molar equivalents, more preferably about 0.5 molar equivalents; and wherein the and when the base is a lithium alkoxide or sodium alkoxide, the base is preferably present in an amount in the range of from about 0.5 to about 3.0 molar equivalents (relative to the moles of the compound of formula (VI), more preferably in an amount in the range of form about 0.5 to about 1.5 molar equivalents, more preferably about 1.0 molar equivalents;

in an organic solvent such as THF, toluene, 2-methyl-THF, MTBE, and the like, preferably THF; preferably at a temperature in the range of from about 0° C. to about room temperature, more preferably at about 0° C.; to yield the corresponding compound of formula (VII).

Preferably, wherein the base is an alkyl lithium such as n-hexyl lithium, and the like, the compound of formula (VI) is added to a mixture of the compound of formula (V) and the organic solvent; followed by addition of the base to the resulting mixture. Preferably, $LG^1$, $LG^2$, the base, the organic solvent and any other reaction conditions are selected to minimize the amount of byproducts.

In an embodiment of the present invention, the compound of formula (V) is reacted with the compound of formula (VI) in the presence of an alkyl lithium, preferably in the presence of n-hexyl lithium. In another embodiment of the present invention, the compound of formula (V) is reacted with the compound of formula (VI) in the presence of a lithium alkoxide, preferably in the presence of lithium methoxide.

The compound of formula (VII) is reacted with a suitably selected aldehyde or ketone derivative of the desired $R^1$ substituent group (more particularly, to a suitably selected aldehyde derivative of $C_{1-4}$alkyl or a suitably selected ketone derivative of $C_{3-10}$cycloalkyl), a known compound or compound prepared by known methods; wherein the aldehyde or ketone derivative of the desired $R^1$ substituent group is preferably present in an amount in the range of from about 1.0 to about 3.0 molar equivalents (relative to the moles of the compound of formula (VII)), more preferably in an amount in the range of from about 1.0 to about 2.0 molar equivalents, more preferably in an amount of about 1.3 molar equivalents;

in the presence of a suitably substituted reducing agent such as sodium triacetoxyborohydride, sodium cyanoborohydride, and the like, preferably sodium triacetoxyborohydride; wherein the reducing agent is preferably present in an amount in the range of from about 1.0 to about 3.0 molar equivalents (relative to the moles of the compound of formula (VII)), more preferably in an amount in the range of from about 1.0 to about 2.0 molar equivalents, more preferably in an amount of about 1.3 molar equivalents;

in an organic solvent such as DCE, THF, 2-methyl-THF, and the like, preferably DCE; preferably at about room temperature; to yield the corresponding compound of formula (X).

Preferably, the aldehyde or ketone derivative of the desired $R^1$ substituent group is added to a mixture of the compound of formula (VII) and the organic solvent, followed by addition of the reducing agent.

In an embodiment, the present invention is directed to a process for the preparation of compounds of formula (X-S) as outlined in more detail in Scheme 2, below.

Scheme 2

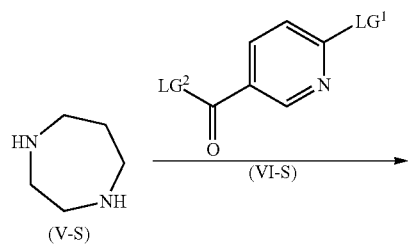

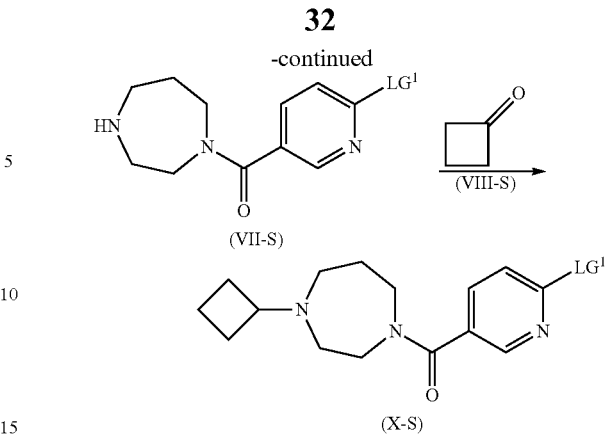

Accordingly, a compound of formula (V-S), a known compound or compound prepared by known methods is reacted with a suitably substituted compound of formula (VI-S), wherein $LG^1$ is a suitably selected first leaving group such as chloro, bromo, fluoro, and the like, preferably chloro, and wherein $LG^2$ is a second leaving group such $OC_{1-4}$alkyl, —O-phenyl, —O-benzyl, chloro, dimethylamino, diethylamino, and the like, preferably —O-methyl or —O— ethyl; wherein the compound of formula (V-S) is present in an amount in the range of from about 1.0 to about 5.0 molar equivalents (relative to moles of the compound of formula (VI-S), more preferably in an amount in the range of from about 2.0 to about 3.0 molar equivalents, more preferably about 2.5 molar equivalents;

in the presence of a suitably selected base such as an alkyl lithium, such as n-hexyl lithium, n-butyl lithium and the like, or in the presence of a suitably selected base such as a lithium alkoxy or sodium alkoxide such as lithium ethoxide, lithium methoxide, sodium methoxide, and the like, or in the presence of a suitably selected base such as isopropyl magnesium chloride, and the like; preferably the base is an alkyl lithium, more preferably, the base is n-hexyl lithium; and when the base is an alkyl lithium, the base is preferably present in an amount in the range of from about 0.1 to about 3.0 molar equivalents (relative to the moles of the compound of formula (VI-S), more preferably in an amount in the range of form about 0.1 to about 1.0 molar equivalents, more preferably about 0.5 molar equivalents; and wherein the and when the base is a lithium alkoxy or sodium alkoxide, the base is preferably present in an amount in the range of from about 0.5 to about 3.0 molar equivalents (relative to the moles of the compound of formula (VI-S), more preferably in an amount in the range of form about 0.5 to about 1.5 molar equivalents, more preferably about 1.0 molar equivalents;

in an organic solvent such as THF, toluene, 2-methyl-THF, MTBE, and the like, preferably THF; preferably at a temperature in the range of from about 000° C. to about room temperature, more preferably at about 0° C.; to yield the corresponding compound of formula (VII-S).

Preferably, wherein the base is an alkyl lithium such as n-hexyl lithium and the like, the compound of formula (VI-S) is added to a mixture of the compound of formula (V-S) and the organic solvent; followed by addition of the base to the resulting mixture. Preferably, $LG^1$, $LG^2$, the base, the organic solvent and any other reaction conditions are selected to minimize the amount of byproducts.

In an embodiment of the present invention, the compound of formula (V-S) is reacted with the compound of formula (VI-S) in the presence of an alkyl lithium, preferably in the presence of n-hexyl lithium. In another embodiment of the present invention, the compound of formula (V-S) is reacted with the compound of formula (VI-S) in the presence of a lithium alkoxide, preferably in the presence of lithium methoxide.

The compound of formula (VII-S) is reacted with a compound of formula (VIII-S) (a suitably selected ketone derivative of the desired $R^1$ substituent group), a known compound or compound prepared by known methods; wherein the compound of formula (VIII-S) is preferably present in an amount in the range of from about 1.0 to about 3.0 molar equivalents (relative to the moles of the compound of formula (VII-S)), more preferably in an amount in the range of from about 1.0 to about 2.0 molar equivalents, more preferably in an amount of about 1.3 molar equivalents;

in the presence of a suitably substituted reducing agent such as sodium triacetoxyborohydride, sodium cyanoborohydride, and the like, preferably sodium triacetoxyborohydride; wherein the reducing agent is preferably present in an amount in the range of from about 1.0 to about 3.0 molar equivalents (relative to the moles of the compound of formula (VII-S)), more preferably in an amount in the range of from about 1.0 to about 2.0 molar equivalents, more preferably in an amount of about 1.3 molar equivalents;

in an organic solvent such as DCE, THF, 2-methyl-THF, and the like, preferably DCE; preferably at about room temperature; to yield the corresponding compound of formula (X-S).

2.0 molar equivalents, more preferably in an amount in the range of from about 1.0 to about 1.5 molar equivalents, more preferably in an amount of about 1.05 molar equivalents; in an organic solvent such as ethanol, acetonitrile, IPA, and the like, preferably ethanol; preferably at a temperature in the range of from about 20° C. to about solvent reflux temperature, more preferably at about 80° C.; to yield the corresponding tartaric acid salt of the compound of formula (IX-S), preferably as a solid; preferably the solid is isolated by filtration;

STEP B: reacting the tartaric acid salt of the compound of formula (X-S) (prepared as in STEP A) with a suitably selected base such as sodium hydroxide, potassium hydroxide, sodium carbonate, and the like, preferably sodium hydroxide; wherein the base is preferably present in an amount in the range of from about 1.0 to about 5.0 molar equivalents, more preferably in an amount in the range of from about 2.5 to about 5.0, more preferably in an amount of about 3.9 molar equivalents; in an organic solvent such as isopropyl acetate, dichloromethane, 2-methyl-THF, and the like; preferably isopropyl acetate; preferably at room temperature; to yield the corresponding compound of formula (X-S).

The present invention is further directed to a process for the preparation of compounds of formula (X) as outlined in more detail in Scheme 3, below.

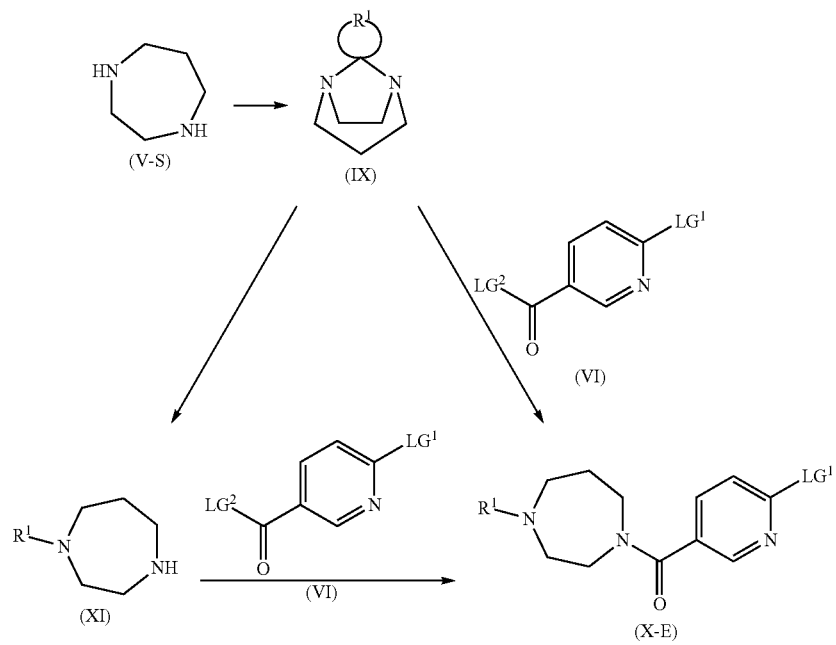

Scheme 3

Preferably, the compound of formula (VIII-S) is added to a mixture of the compound of formula (VII-S) and the organic solvent, followed by addition of the reducing agent.

In an embodiment, the present invention is directed to a process for the purification of the compound of formula (X-S), which process comprising the following steps:

STEP A: reacting the compound of formula (X-S) with L-tartaric acid; wherein the L-tartaric acid is preferably present in an amount in the range of form about 0.5 to about Accordingly, a suitably substituted compound of formula (V-S), a known compound or compound prepared by known methods, is reacted with a suitably selected aldehyde or ketone derivative of the desired $R^1$ substituent group (more particularly, with a suitably selected aldehyde or ketone derivative of $C_{1-4}$ alkyl or a suitably selected ketone derivative of $C_{3-10}$cycloalkyl), wherein the suitably selected aldehyde or ketone derivative of the desired $R^1$ substituent group is preferably present in an amount in the range of from about 0.5 to about 2.0 molar equivalents (relative to the moles of the compound of formula (V-S)), more preferably in an amount in the range of from about 1.0 to about 1.5 molar equivalents, more preferably in an amount of about 1.05 molar equivalents;

neat or in an organic solvent such as toluene, THF, 2-methyl-THF, hexane, and the like, preferably toluene; preferably at a temperature in the range of from about room temperature to about reflux temperature, more preferably at an elevated temperature of greater than about 40° C., more preferably at about reflux temperature; to yield the corresponding compound of formula (IX).

The compound of formula (IX) is reacted with a suitably selected reducing agent such as sodium borohydride, potassium borohydride, lithium borohydride, sodium triacetoxyborohydride, and the like, preferably sodium borohydride; wherein the reducing agent is preferably present in an amount in the range of from about 0.5 to about 1.5 molar equivalents (relative to the amount of the compound of formula (IX), more preferably in an amount of about 1.0 molar equivalents; wherein the reducing agent is preferably added as a solution in water, stabilized with a suitably selected base such as sodium hydroxide in an amount of about 0.1 equivalents;

optionally in the presence of an acid such as HCl, acetic acid, sulfuric acid, trifluoroacetic acid, and the like, preferably HCl; preferably, the acid is not substantially reduced under the conditions of the reaction, more preferably, the acid is not reduced under the conditions of the reaction; wherein the acid is preferably present in an amount in the range of from about 1.0 to about 5.0 molar equivalents (relative to the moles of the compound of formula (IX)), more preferably in an amount in the range of from about 3.0 to about 5.0 molar equivalents, more preferably in an amount of about 4.0 molar equivalents;

neat, in water or an aqueous organic solvent such as methanol, ethanol, isopropanol, THF, acetonitrile, and the like; preferably at a temperature in the range of from about −10° C. to about 000° C., more preferably at about −5° C.; to yield the corresponding compound of formula (XI).

Preferably, wherein the reducing agent is lithium borohydride, the compound of formula (IX) is reacted with the reducing agent in the absence of the acid.

The compound of formula (XI) is reacted with a suitably substituted compound of formula (VI), wherein $LG^1$ is a suitably selected first leaving group such as chloro, bromo, fluoro, and the like, preferably chloro, and wherein $LG^2$ is a second leaving group such O—$C_{1-4}$alkyl, —O-phenyl, —O-benzyl, chloro, fluoro, bromo, and the like, preferably chloro; wherein preferably, $LG^2$ is more reactive than $LG^1$ under the reaction conditions; and wherein the compound of formula (VI) is present in an amount in the range of from about 0.5 to about 2.0 molar equivalents (relative to moles of the compound of formula (IX)), more preferably in an amount in the range of from about 1.0 to about 1.5 molar equivalents, more preferably about 1.05 molar equivalents;

in an organic solvent such as MTBE, toluene, THF, 2-methyl-THF, and the like, preferably toluene or 2-methyl-THF; preferably at a temperature in the range of from about room temperature to about 50° C., more preferably at a temperature in the range of form about 0° C. to about 35° C.; to yield the corresponding compound of formula (X-E).

Alternatively, the compound of formula (XI), is reacted with a suitably substituted compound of formula (VI), wherein $LG^1$ is a suitably selected first leaving group such as chloro, bromo, fluoro, and the like, preferably chloro, and wherein $LG^2$ is a second leaving group such O-$C_{1-4}$alkyl, —O-phenyl, —O-benzyl, chloro, fluoro, bromo, and the like, preferably chloro; wherein preferably, $LG^2$ is more reactive than $LG^1$ under the reaction conditions; and wherein the compound of formula (VI) is present in an amount in the range of from about 0.5 to about 2.0 molar equivalents (relative to moles of the compound of formula (IX)), more preferably in an amount in the range of from about 1.0 to about 1.5 molar equivalents, more preferably about 1.05 molar equivalents;

in the presence of a suitably selected base, preferably a suitably selected inorganic base such as NaOH, KOH, LiOH, sodium carbonate, potassium carbonate, cesium carbonate, sodium phosphate, potassium phosphate, and the like, more preferably NaOH, more preferably 30% NaOH; wherein the base is preferably present in an amount greater than 1 molar equivalent (relative to the moles of the compound of formula (VI)), more preferably in an amount in the range of from about 1.05 to about 2.5 molar equivalents, more preferably in an amount in the range of from about 1.5 to about 2 molar equivalents;

in a mixture of water and a suitably selected organic solvent such as MTBE, 2-methyl-THF, toluene, and the like; preferably at a temperature of less than about 30° C., more preferably at a temperature in the range of from about 0° C. to about 20° C., more preferably at a temperature in the range of about 10° C. to about 15° C.; to yield the corresponding compound of formula (X).

Preferably, the compound of formula (VI) in a suitably selected solvent is added to an aqueous solution of the compound of formula (XI) and the base. More preferably, the compound of formula (VI) in MTBE is added to an aqueous solution of the compound of formula (XI) and 30% NaOH.

One skilled in the art will recognize that when in the compound of formula (VI) $LG^2$ is chloro, then the compound of formula (X-E) is prepared as its corresponding HCl salt. Further, alternate suitable $LG^2$ leaving groups may be selected, as would be readily understood and recognized by one skilled in the art, to yield the compound of formula (X-E) as the corresponding salt forms.

Alternatively, the compound of formula (IX) is reacted with a suitably substituted compound of formula (VI), wherein $LG^1$ is a suitably selected first leaving group such as chloro, bromo, fluoro, and the like, preferably chloro, and wherein $LG^2$ is a second leaving group such O-$C_{1-4}$alkyl, —O-phenyl, —O-benzyl, chloro, fluoro, bromo, and the like, preferably chloro; and wherein $LG^2$ is preferably more reactive than $LG^1$ under the reaction conditions, a known compound or compound prepared by known methods; wherein the compound of formula (VI) is present in an amount in the range of from about 0.5 to about 2.0 molar equivalents (relative to moles of the compound of formula (IX), more preferably in an amount in the range of from about 1.0 to about 1.5 molar equivalents, more preferably about 1.05 molar equivalents;

in the presence of a suitably selected reducing agent such as sodium triacetoxyborohydride, sodium cyanoborohydride, sodium borohydride, and the like, preferably sodium triacetoxyborohydride; wherein the reducing agent is preferably present in an amount in the range of from about 0.5 to about 2.0 molar equivalents (relative to the moles of the compound of formula (IX)), more preferably in an amount in the range of from about 1.0 to about 1.5 molar equivalents, more preferably in an amount of about 1.25 molar equivalents;

optionally in the presence of an organic acid such as TFA, acetic acid, and the like, preferably acetic acid; wherein the acid is preferably present in an amount in the range of form about 0.5 to about 2.0 molar equivalents (relative to the moles of the compound of formula (IX)), more preferably in an amount in the range of from about 0.5 to about 1.5 molar equivalents, more preferably in an amount of about 1.0 molar equivalents;

in an organic solvent such as toluene, THF, acetonitrile, and the like, preferably acetonitrile; preferably at a temperature in the range of from about room temperature to about 50° C., more preferably at a temperature in the range of from about room temperature to about 35° C.; to yield the corresponding compound of formula (X-E).

Preferably, the compound of formula (VI) is added to a mixture of the compound of formula (IX) and the reducing agent, in the organic solvent.

In an embodiment, the present invention is directed to a process for the preparation of compounds of formula (X-S) as outlined in more detail in Scheme 4, below.

The compound of formula (IX-S) is reacted with a suitably selected reducing agent such as sodium borohydride, potassium borohydride, lithium borohydride, sodium triacetoxyborohydride, and the like, preferably sodium borohydride; wherein the reducing agent is preferably present in an amount in the range of from about 0.5 to about 1.5 molar equivalents (relative to the amount of the compound of formula (IX-S), more preferably in an amount of about 1.0 molar equivalents; wherein the reducing agent is preferably added as a solution in water, stabilized with a suitably selected base such as sodium hydroxide in an amount of about 0.1 equivalents;

optionally in the presence of an acid such as HCl, acetic acid, sulfuric acid, trifluoroacetic acid, and the like, preferably HCl; preferably, the acid is not substantially reduced under the conditions of the reaction, more preferably, the acid is not reduced under the conditions of the reaction; wherein the acid is preferably present in an amount in the

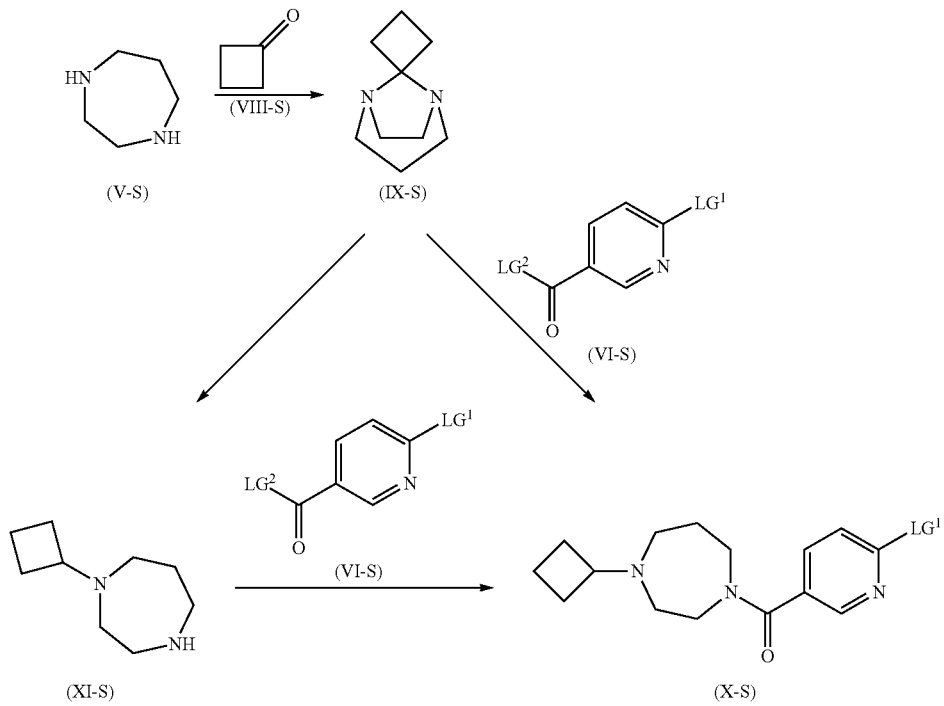

Scheme 4 range of from about 1.0 to about 5.0 molar equivalents (relative to the moles of the compound of formula (IX-S)), more preferably in an amount in the range of from about 3.0 to about 5.0 molar equivalents, more preferably in an amount of about 4.0 molar equivalents;

neat, in water or an aqueous organic solvent such as methanol, ethanol, IPA, THF, acetonitrile, and the like; preferably at a temperature in the range of from about −10° C. to about 0° C., more preferably at about −5° C.; to yield the corresponding compound of formula (XI-S).

Preferably, wherein the reducing agent is lithium borohydride, the compound of formula (IX) is reacted with the reducing agent in the absence of the acid.

The compound of formula (XI-S) is reacted with a suitably substituted compound of formula (VI-S), wherein $LG^1$ is a suitably selected first leaving group such as chloro, bromo, fluoro, and the like, preferably chloro, and wherein Accordingly, a compound of formula (V-S), a known compound or compound prepared by known methods, is reacted with a compound of formula (VIII-S) (a suitably selected ketone derivative of the desired $R^1$ substituent group), wherein the compound of formula (VIII-S) is preferably present in an amount in the range of from about 0.5 to about 2.0 molar equivalents (relative to the moles of the compound of formula (V-S)), more preferably in an amount in the range of from about 1.0 to about 1.5 molar equivalents, more preferably in an amount of about 1.05 molar equivalents;

neat or in an organic solvent such as toluene, THF, 2-methyl-THF, hexane, and the like, preferably toluene; preferably at a temperature in the range of from about room temperature to about reflux temperature, more preferably at an elevated temperature of greater than about 40° C., more preferably at about reflux temperature; to yield the corresponding compound of formula (IX-S).

$LG^2$ is a second leaving group such $O-C_{1-4}$alkyl, —O-phenyl, —O-benzyl, chloro, fluoro, bromo, and the like, preferably chloro; wherein preferably, $LG^2$ is more reactive than $LG^1$ under the reaction conditions; and wherein the compound of formula (VI-S) is present in an amount in the range of from about 0.5 to about 2.0 molar equivalents (relative to moles of the compound of formula (IX-S)), more preferably in an amount in the range of from about 1.0 to about 1.5 molar equivalents, more preferably about 1.05 molar equivalents;

in an organic solvent such as MTBE, toluene, THF, 2-methyl-THF, and the like, preferably toluene or 2-methyl-THF; preferably at a temperature in the range of from about room temperature to about 50° C., more preferably at a temperature in the range of form about 0° C. to about 35° C.; to yield the corresponding compound of formula (X-S).

One skilled in the art will recognize that when in the compound of formula (VI-S) $LG^2$ is chloro, then the compound of formula (X-S) is prepared as its corresponding HCl salt. Further, alternate suitable $LG^2$ leaving groups may be selected, as would be readily understood and recognized by one skilled in the art, to yield the compound of formula (X-E) as the corresponding salt forms.

Alternatively, the compound of formula (XI-S), is reacted with a suitably substituted compound of formula (VI-S), wherein $LG^1$ is a suitably selected first leaving group such as chloro, bromo, fluoro, and the like, preferably chloro, and wherein $LG^2$ is a second leaving group such $O-C_{1-4}$alkyl, —O-phenyl, —O-benzyl, chloro, fluoro, bromo, and the like, preferably chloro; wherein preferably, $LG^2$ is more reactive than $LG^1$ under the reaction conditions; and wherein the compound of formula (VI-S) is present in an amount in the range of from about 0.5 to about 2.0 molar equivalents (relative to moles of the compound of formula (IX-S)), more preferably in an amount in the range of from about 1.0 to about 1.5 molar equivalents, more preferably about 1.05 molar equivalents;

in the presence of a suitably selected base, preferably a suitably selected inorganic base such as NaOH, KOH, LiOH, sodium carbonate, potassium carbonate, cesium carbonate, sodium phosphate, potassium phosphate, and the like, more preferably NaOH, more preferably 30% NaOH; wherein the base is preferably present in an amount greater than 1 molar equivalent (relative to the moles of the compound of formula (VI-S)), more preferably in an amount in the range of from about 1.05 to about 2.5 molar equivalents, more preferably in an amount in the range of from about 1.5 to about 2 molar equivalents;

in a mixture of water and a suitably organic selected solvent such as MTBE, 2-methylTHF, toluene, and the like; preferably at a temperature of less than about 30° C., more preferably at a temperature in the range of from about 0° C. to about 20° C., more preferably at a temperature in the range of about 10° C. to about 15° C.; to yield the corresponding compound of formula (X-S).

Preferably, the compound of formula (VI-S) in a suitably selected solvent is added to an aqueous solution of the compound of formula (XI-S) and the base. More preferably, the compound of formula (VI-S) in MTBE is added to an aqueous solution of the compound of formula (XI-S) and 30% NaOH.

Alternatively, the compound of formula (IX-S) is reacted with a suitably substituted compound of formula (VI-S), wherein $LG^1$ is a suitably selected first leaving group such as chloro, bromo, fluoro, and the like, preferably chloro, and wherein $LG^2$ is a second leaving group such $O-C_{1-4}$alkyl, —O-phenyl, —O-benzyl, chloro, fluoro, bromo, and the like, preferably chloro; and wherein $LG^2$ is preferably more reactive than $LG^1$ under the reaction conditions, a known compound or compound prepared by known methods; wherein the compound of formula (VI-S) is present in an amount in the range of from about 0.5 to about 2.0 molar equivalents (relative to moles of the compound of formula (IX-S)), more preferably in an amount in the range of from about 1.0 to about 1.5 molar equivalents, more preferably about 1.05 molar equivalents;

in the presence of a suitably selected reducing agent such as sodium triacetoxyborohydride, sodium cyanoborohydride, sodium borohydride, and the like, preferably sodium triacetoxyborohydride; wherein the reducing agent is preferably present in an amount in the range of from about 0.5 to about 2.0 molar equivalents (relative to the moles of the compound of formula (IX-S)), more preferably in an amount in the range of from about 1.0 to about 1.5 molar equivalents, more preferably in an amount of about 1.25 molar equivalents;

optionally in the presence of an organic acid such as TFA, acetic acid, and the like, preferably acetic acid; wherein the acid is preferably present in an amount in the range of form about 0.5 to about 2.0 molar equivalents (relative to the moles of the compound of formula (IX-S)), more preferably in an amount in the range of from about 0.5 to about 1.5 molar equivalents, more preferably in an amount of about 1.0 molar equivalents;

in an organic solvent such as toluene, THF, acetonitrile, and the like, preferably acetonitrile; preferably at a temperature in the range of from about room temperature to about 50° C., more preferably at a temperature in the range of from about room temperature to about 35° C.; to yield the corresponding compound of formula (X-S).

Preferably, the compound of formula (VI-S) is added to a mixture of the compound of formula (IX-S) and the reducing agent, in the organic solvent.

Preferably, wherein the compound of formula (X-S) is prepared as a free base, the compound of formula (X-S) may be reacted with for example anhydrous HCl (or HCl gas), wherein the anhydrous HCl is dissolved in a suitably selected organic solvent such as 2-propanol, diethyl ether, and the like, preferably 2-propanol, to yield the corresponding compound of formula (X-S), as its corresponding HCl salt, preferably as a solid.

The present invention is further directed to processes for the preparation of compounds of formula (I), as outlined in more detail in Scheme 5, below.

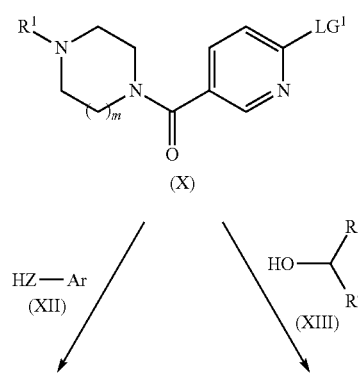

-continued

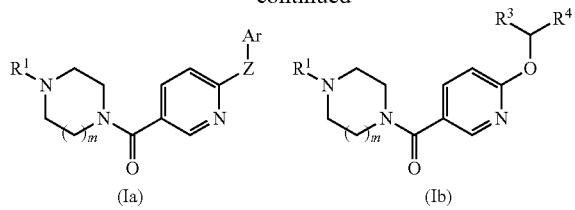

(Ia)    (Ib)

Accordingly, a suitably substituted compound of formula (X) or its corresponding pharmaceutically acceptable salt, prepared as for example described herein, is reacted with a compound of formula (XII), a known compound or compound prepared by known methods; wherein the compound of formula (XII) is preferably present in an amount in the range of from about 0.5 to about 2.0 molar equivalents (relative to the moles of the compound of formula (X), more preferably in an amount in the range of from about 1.0 to about 2.0 molar equivalents, more preferably in an amount of about 1.1 to about 1.5 molar equivalents;

in the presence of a suitably selected first inorganic base such as cesium carbonate, potassium carbonate, and the like, preferably cesium carbonate; wherein the inorganic base is preferably present in an amount in the range of from about 1.5 to about 3.0 molar equivalents (relative to the moles of the compound of formula (X), more preferably in an amount of about 2.0 molar equivalents;

in an organic solvent such as DMA, DMF, NMP, acetonitrile, and the like, preferably DMA; preferably at a temperature in the range of from about 75° C. to about reflux temperature, more preferably at a temperature in the range of form about 90° C. to about 125° C.; to yield the corresponding compound of formula (Ia).

Preferably the compound of formula (Ia) is further reacted with a suitably selected acid such as HCl; in an organic solvent such as IPA; to yield the corresponding acid addition salt of the compound of formula (Ia).

Alternatively, a suitably substituted compound of formula (X), prepared as for example described herein, is reacted with a compound of formula (XIII), a known compound or compound prepared by known methods; wherein the compound of formula (XIII) is preferably present in an amount in the range of from about 1.0 to about 3.0 molar equivalents (relative to the moles of the compound of formula (X)), more preferably in an amount of about 1.2 molar equivalents;

in the presence of a suitably selected second inorganic base such as KOH, KO-t-Bu, NaOH, NaO-t-Bu, and the like, preferably KOH; wherein the inorganic base is preferably present in an amount in the range of from 1.0 to about 5.0 molar equivalents (relative to the moles of the compound of formula (X)), more preferably in an amount in the range of from about 2.0 to about 4.0 molar equivalents, more preferably in an amount of about 3.3 molar equivalents;

optionally in the presence of a suitably selected additive such as a suitably selected crown ether such as 18-crown-6, or a suitably selected additive such as diglyme, and the like; wherein the additive is preferably present in a catalytic amount;

in an organic solvent such as toluene, THF, 2-methyl-THF, and the like, preferably toluene; preferably at a temperature in the range of from 60° C. to about reflux temperature, more preferably at about reflux temperature; to yield the corresponding compound of formula (Ib).

Preferably the compound of formula (Ib) is further reacted with a suitably selected acid such as HCl; in an organic solvent such as IPA; to yield the corresponding acid addition salt of the compound of formula (Ib).

In certain embodiments, the present invention is directed to processes for the preparation of compound (I-A) and compound (I-B), as outlined in more detail in Scheme 6, below.

Scheme 6

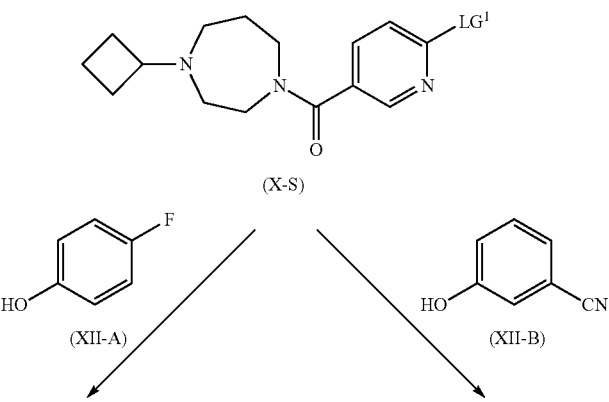

(X-S)

(XII-A)    (XII-B)

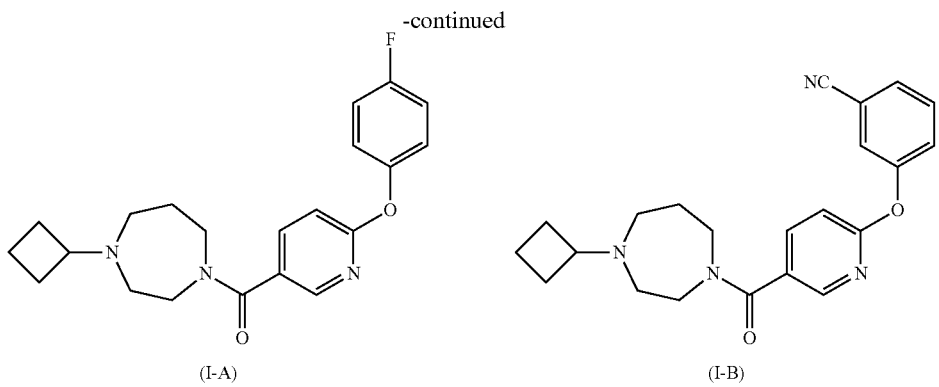

(I-A)                              (I-B)

Accordingly, a suitably substituted compound of formula (X-S) or its corresponding pharmaceutically acceptable salt thereof, preferably the corresponding HCl salt of the compound of formula (X-S), prepared as for example described herein, is reacted with a compound of formula (XII-A), a known compound or compound prepared by known methods; wherein the compound of formula (XII-A) is preferably present in an amount in the range of from about 0.5 to about 2.0 molar equivalents (relative to the moles of the compound of formula (X-S)), more preferably in an amount in the range of from about 1.0 to about 2.0 molar equivalents, more preferably in an amount of about 1.1 to about 1.5 molar equivalents;

in the presence of a suitably selected first inorganic base such as cesium carbonate, potassium carbonate, and the like, preferably cesium carbonate; wherein the inorganic base is preferably present in an amount in the range of from about 1.5 to about 3.0 molar equivalents (relative to the moles of the compound of formula (X-S)), more preferably in an amount of about 2.0 molar equivalents;

in an organic solvent such as DMA, DMF, NMP, acetonitrile, and the like, preferably DMA or DMF; preferably at a temperature in the range of from about 75° C. to about reflux temperature, more preferably at a temperature in the range of form about 90° C. to about 125° C.; to yield the corresponding compound (I-A).

Preferably compound (I-A) is further reacted with a suitably selected acid such as HCl; in an organic solvent such as IPA; to yield the corresponding salt of compound (I-A).

Alternatively, a suitably substituted compound of formula (X-S), prepared as for example described herein, is reacted with a compound of formula (XII-B), a known compound or compound prepared by known methods; wherein the compound of formula (XII-B) is preferably present in an amount in the range of from about 0.5 to about 2.0 molar equivalents (relative to the moles of the compound of formula (X-S)), more preferably in an amount in the range of from about 1.0 to about 2.0 molar equivalents, more preferably in an amount of about 1.1 to about 1.5 molar equivalents;

in the presence of a suitably selected first inorganic base such as cesium carbonate, potassium carbonate, and the like, preferably cesium carbonate; wherein the inorganic base is preferably present in an amount in the range of from about 1.5 to about 3.0 molar equivalents (relative to the moles of the compound of formula (X-S)), more preferably in an amount of about 2.5 molar equivalents;

in an organic solvent such as DMA, DMF, NMP, acetonitrile, and the like, or mixture thereof, preferably DMA or a mixture of DMA and acetonitrile; preferably at a temperature in the range of from about 75° C. to about reflux temperature, more preferably at a temperature in the range of form about 90° C. to about 125° C.; to yield the corresponding compound (I-B).

Preferably compound (I-B) is further reacted with a suitably selected acid such as HCl; in an organic solvent or mixture of organic solvents, such as IPA or a mixture of IPA and ethylmethylketone; to yield the corresponding salt of compound (I-B).

In another embodiment, the present invention is directed to processes for the preparation of compound (I-C), as outlined in more detail in Scheme 7, below.

Scheme 7

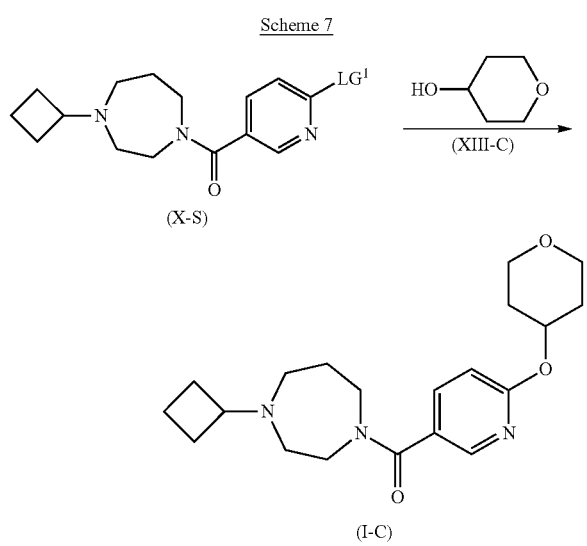

(I-C)

Accordingly, a suitably substituted compound of formula (X-S), prepared as described herein, is reacted with a compound of formula (XIII-C), a known compound or compound prepared by known methods; wherein the compound of formula (XIII-C) is preferably present in an amount in the range of from about 1.0 to about 3.0 molar equivalents (relative to the moles of the compound of formula (X-S)), more preferably in an amount in the range of from about 1.1 to about 1.5 molar equivalents, more preferably, in an amount of about 1.2 molar equivalents;

in the presence of a suitably selected second inorganic base such as KOH, KO-t-Bu, NaOH, NaO-t-Bu, and the like, preferably KOH; wherein the inorganic base is preferably present in an amount in the range of from about 1.0 to about 5.0 molar equivalents (relative to the moles of the compound of formula (X-S)), more preferably in an amount in the range of from about 2.0 to about 4.0 molar equivalents, more preferably, in an amount of about 3.3 molar equivalents;

optionally in the presence of a suitably selected additive such as a suitably selected crown ether such as 18-crown-6, or a suitably selected additive such as diglyme, and the like; wherein the additive is preferably present in a catalytic amount;

in an organic solvent such as toluene, THF, 2-methyl-THF, and the like, or a mixture of organic solvent and water, preferably toluene; preferably at a temperature in the range of from 60° C. to about reflux temperature, more preferably at about reflux temperature; to yield the corresponding compound (I-C).

Alternatively, a suitably substituted compound of formula (X-S), present as its corresponding pharmaceutically acceptable salt, preferably as its corresponding HCl salt, prepared as for example described herein, is reacted with a suitably selected first inorganic base such as sodium carbonate, potassium carbonate, sodium hydroxide, potassium hydroxide, sodium bicarbonate, potassium bicarbonate, and the like, preferably sodium carbonate; wherein the base is present in an amount in the range of from about 1.0 to about 2.0 molar equivalents (relative to the moles of the compound of formula (X-S), more preferably, in an amount of about 1.5 molar equivalents; to liberate the free base of the compound of formula (X-S)); wherein the resulting salt is preferably removed from the resulting biphasic mixture in the aqueous layer;

the liberated free base of the compound of formula (X-S) is then reacted with a compound of formula (XIII-C), a known compound or compound prepared by known methods; wherein the compound of formula (XIII-C) is preferably present in an amount in the range of from about 1.0 to about 3.0 molar equivalents (relative to the moles of the compound of formula (X-S)), more preferably in an amount of about 1.2 molar equivalents;

in the presence of a suitably selected second inorganic base such as KOH, KO-t-Bu, NaOH, NaO-t-Bu, and the like, preferably KOH; wherein the inorganic base is preferably present in an amount in the range of from 1.0 to about 5.0 molar equivalents (relative to the moles of the compound of formula (X-S)), more preferably in an amount in the range of from about 2.0 to about 4.0 molar equivalents, more preferably, in an amount of about 3.3 equivalents;

optionally in the presence of a suitably selected additive such as a suitably selected crown ether such as 18-crown-6 (also known as 1,4,7,10,13,16-hexaoxacyclooctadecane), or a suitably selected additive such as diglyme (also known as bis(2-methoxyethyl) ether), and the like; wherein the additive is preferably present in a catalytic amount;

in an organic solvent such as toluene, THF, 2-methyl-THF, and the like, or a mixture of organic solvent and water, preferably toluene; preferably at a temperature in the range of from 60° C. to about reflux temperature, more preferably at about reflux temperature; to yield the corresponding compound (I-C).

Preferably compound (I-C) is further reacted with a suitably selected acid such as anhydrous HCl; in an organic solvent such as IPA, and the like; to yield the corresponding salt of compound (I-C).

Figure 2:
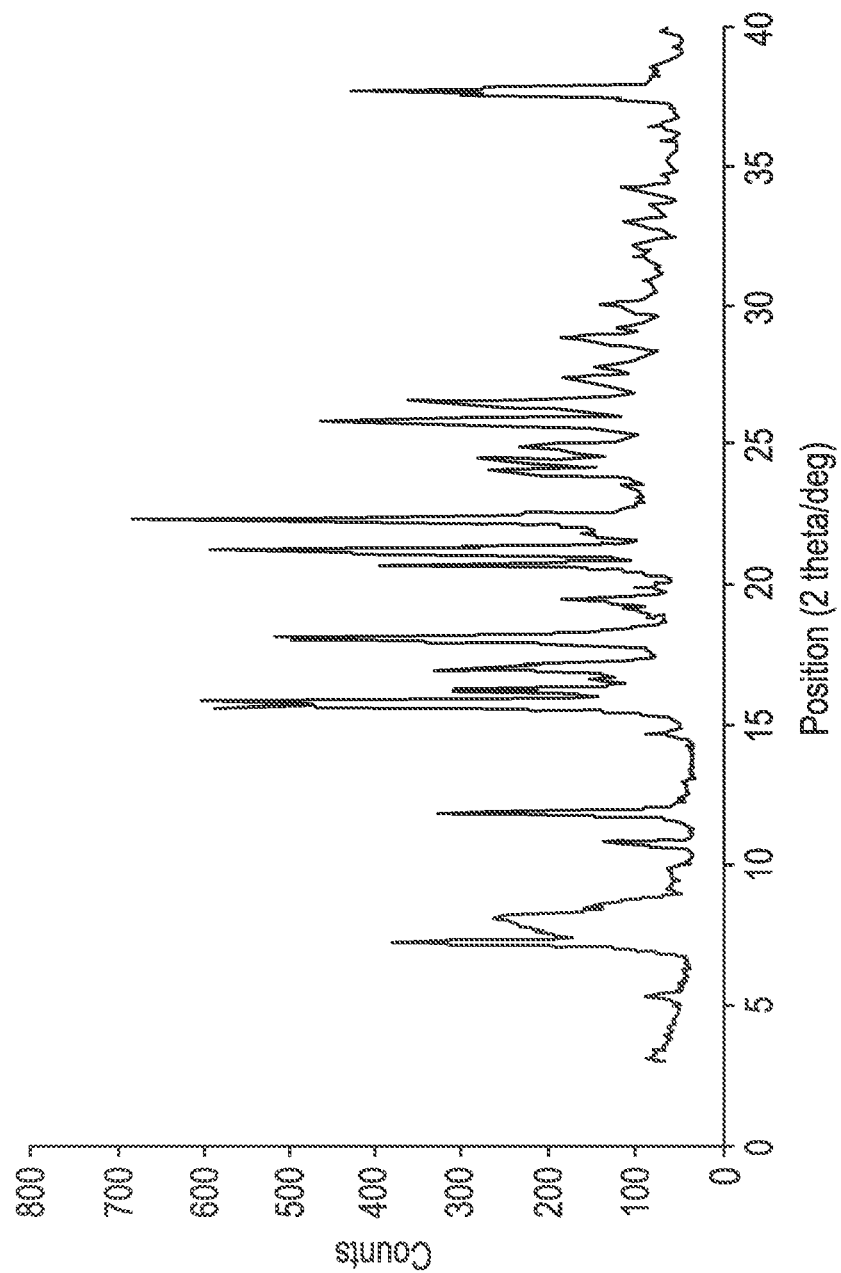
FIG. 2 illustrates a powder XRD spectrum for the crystalline HCl salt of compound (I-B), FORM II.

The present invention is further directed to two novel crystalline HCl salts of compound (I-B), more particularly FORM I and FORM II. A representative powder X-ray diffraction (XRD) spectra of the crystalline HCl salt of compound (I-B) FORM I is shown in FIG. 1. A representative powder X-ray diffraction (XRD) spectra of the crystalline HCl salt of compound (I-B) FORM II is shown in FIG. 2. The present invention is further directed to a novel crystalline HCl salt of compound (I-C). A representative powder XRD spectra of the crystalline HCl salt of compound (I-C) is shown in FIG. 3.

The powder XRD spectrum of a representative sample of the crystalline HCl salt of compound (I-B) FORM I and a representative sample of the crystalline HCl salt of compound (I-C) was measured using an XPERT-PRO diffractometer system. The sample was back-loaded into a conventional x-ray holder, at 25° C. The sample was scanned from 4 to 41° 2θ with a step size of 0.0170° 2θ and a time per step of 17.44 seconds. Instrument voltage and current settings were 45 kV and 40 mA.

The powder XRD spectrum of a representative sample of the crystalline HCl salt of compound (I-B) FORM II was measured using a computer controlled powder diffractometer system (APD2000 by G. N. R. s. r. l.). The sample was back-loaded into an X-ray holder for automatic sample changer, at 25° C. The sample was scanned from 3 to 40°2θ with a step size of 0.01° 2θ and a time per step of 5 seconds. Instrument voltage and current settings were 40 kV and 30 mA.

The crystalline HCl salt of compound (I-B) FORM I, may be characterized by its X-ray diffraction pattern, comprising the peaks as listed in Table 1, below.

TABLE 1

Powder XRD Peaks, HCl Salt of Compound (I-B), FORM I

| Position [°2θ] | d-spacing [Å] | Relative Intensity (%) |
|---|---|---|
| 9.95 | 8.89 | 55 |
| 10.98 | 8.06 | 10 |
| 12.64 | 7.00 | 58 |
| 16.06 | 5.52 | 100 |
| 16.78 | 5.29 | 87 |
| 17.83 | 4.98 | 100 |
| 18.68 | 4.75 | 41 |
| 19.13 | 4.64 | 50 |
| 19.89 | 4.47 | 46 |
| 20.97 | 4.24 | 97 |
| 22.01 | 4.04 | 14 |
| 23.00 | 3.87 | 32 |
| 23.60 | 3.77 | 17 |
| 24.38 | 3.65 | 17 |
| 25.34 | 3.51 | 48 |
| 25.99 | 3.43 | 53 |
| 26.72 | 3.34 | 28 |
| 27.71 | 3.22 | 35 |
| 28.36 | 3.15 | 15 |
| 31.90 | 2.81 | 18 |
| 32.42 | 2.76 | 16 |

Preferably, the crystalline HCl salt of compound (I-B), FORM I is characterized by its powder XRD pattern, which comprises peaks having a relative intensity greater than or equal to about 20%, as listed in Table 2 below.

TABLE 2

Powder XRD Peaks, HCl Salt of Compound (I-B), FORM I

| Position [°2θ] | d-spacing [Å] | Relative Intensity (%) |
|---|---|---|
| 9.95 | 8.89 | 55 |
| 12.64 | 7.00 | 58 |
| 16.06 | 5.52 | 100 |
| 16.78 | 5.29 | 87 |
| 17.83 | 4.98 | 100 |
| 18.68 | 4.75 | 41 |

TABLE 2-continued

Powder XRD Peaks, HCl Salt of Compound (I-B), FORM I

| Position [°2θ] | d-spacing [Å] | Relative Intensity (%) |
|---|---|---|
| 19.13 | 4.64 | 50 |
| 19.89 | 4.47 | 46 |
| 20.97 | 4.24 | 97 |
| 23.00 | 3.87 | 32 |
| 25.34 | 3.51 | 48 |
| 25.99 | 3.43 | 53 |
| 26.72 | 3.34 | 28 |
| 27.71 | 3.22 | 35 |

More preferably, the crystalline HCl salt of compound (I-B), FORM I is characterized by its powder XRD pattern, which comprises peaks having a relative intensity greater than or equal to about 25%, more preferably greater than or equal to about 50%.

The crystalline HCl salt of compound (I-B) FORM II, may be characterized by its X-ray diffraction pattern, comprising the peaks as listed in Table 3, below.

TABLE 3

Powder XRD Peaks, HCl Salt of Compound (I-B), FORM II

| Position [°2θ] | d-spacing [Å] | Relative Intensity (%) |
|---|---|---|
| 5.32 | 16.60 | 13 |
| 7.29 | 12.12 | 55 |
| 10.79 | 8.19 | 20 |
| 11.90 | 7.43 | 48 |
| 14.75 | 6.00 | 13 |
| 15.79 | 5.61 | 72 |
| 15.92 | 5.56 | 88 |
| 16.29 | 5.44 | 45 |
| 16.72 | 5.30 | 22 |
| 17.04 | 5.20 | 46 |
| 17.22 | 5.15 | 33 |
| 18.17 | 4.88 | 76 |
| 18.79 | 4.72 | 12 |
| 19.15 | 4.63 | 15 |
| 19.53 | 4.54 | 26 |
| 19.98 | 4.44 | 15 |
| 20.75 | 4.28 | 57 |
| 21.32 | 4.16 | 86 |
| 21.82 | 4.07 | 24 |
| 22.42 | 3.96 | 100 |
| 23.42 | 3.80 | 16 |
| 24.05 | 3.70 | 39 |
| 24.49 | 3.63 | 40 |
| 24.78 | 3.59 | 27 |
| 25.01 | 3.56 | 34 |
| 25.9 | 3.44 | 67 |
| 26.58 | 3.35 | 53 |
| 27.42 | 3.25 | 27 |
| 27.83 | 3.20 | 21 |
| 28.78 | 3.10 | 26 |
| 29.00 | 3.08 | 18 |
| 30.08 | 2.97 | 20 |
| 30.87 | 2.89 | 12 |
| 31.94 | 2.80 | 14 |
| 33.03 | 2.71 | 16 |
| 33.58 | 2.67 | 13 |
| 34.19 | 2.62 | 16 |

Preferably, the crystalline HCl salt of compound (I-B), FORM II is characterized by its powder XRD pattern, which comprises peaks having a relative intensity greater than or equal to about 25%, as listed in Table 4 below.

TABLE 4

Powder XRD Peaks, HCl Salt of Compound (I-B), FORM II

| Position [°2θ] | d-spacing [Å] | Relative Intensity (%) |
|---|---|---|
| 7.29 | 12.12 | 55 |
| 11.90 | 7.43 | 48 |
| 15.79 | 5.61 | 72 |
| 15.92 | 5.56 | 88 |
| 16.29 | 5.44 | 45 |
| 17.04 | 5.20 | 46 |
| 17.22 | 5.15 | 33 |
| 18.17 | 4.88 | 76 |
| 19.53 | 4.54 | 26 |
| 20.75 | 4.28 | 57 |
| 21.32 | 4.16 | 86 |
| 22.42 | 3.96 | 100 |
| 24.05 | 3.70 | 39 |
| 24.49 | 3.63 | 40 |
| 24.78 | 3.59 | 27 |
| 25.01 | 3.56 | 34 |
| 25.90 | 3.44 | 67 |
| 26.58 | 3.35 | 53 |
| 27.42 | 3.25 | 27 |
| 28.78 | 3.10 | 26 |

More preferably, the crystalline HCl salt of compound (I-B), FORM II is characterized by its powder XRD pattern, which comprises peaks having a relative intensity greater than or equal to about 50%.

The crystalline HCl salt of compound (I-C), may be characterized by its X-ray diffraction pattern, comprising the peaks as listed in Table 5, below.

TABLE 5

Powder XRD Peaks, HCl Salt of Compound (I-C)

| Position [°2θ] | d-spacing [Å] | Relative Intensity (%) |
|---|---|---|
| 8.13 | 10.87 | 59 |
| 14.76 | 6.00 | 24 |
| 15.66 | 5.66 | 27 |
| 16.28 | 5.44 | 55 |
| 17.71 | 5.01 | 100 |
| 18.06 | 4.91 | 56 |
| 19.20 | 4.62 | 39 |
| 19.62 | 4.52 | 36 |
| 20.57 | 4.32 | 12 |
| 21.27 | 4.18 | 12 |
| 21.88 | 4.06 | 30 |
| 23.35 | 3.81 | 70 |
| 24.40 | 3.65 | 42 |
| 24.67 | 3.61 | 58 |
| 26.36 | 3.38 | 28 |
| 29.46 | 3.03 | 25 |
| 31.60 | 2.83 | 23 |
| 32.54 | 2.75 | 17 |

Preferably, the crystalline HCl salt of compound (I-C) is characterized by its powder XRD pattern, which comprises peaks having a relative intensity greater than or equal to about 20%, as listed in Table 6 below.

TABLE 6

Powder XRD Peaks, HCl Salt of Compound (I-C)

| Position [°2θ] | d-spacing [Å] | Relative Intensity (%) |
|---|---|---|
| 8.13 | 10.87 | 59 |
| 14.76 | 6.00 | 24 |
| 15.66 | 5.66 | 27 |
| 16.28 | 5.44 | 55 |
| 17.71 | 5.01 | 100 |
| 18.06 | 4.91 | 56 |

TABLE 6-continued

Powder XRD Peaks, HCl Salt of Compound (I-C)

| Position [°2θ] | d-spacing [Å] | Relative Intensity (%) |
|---|---|---|
| 19.20 | 4.62 | 39 |
| 19.62 | 4.52 | 36 |
| 21.88 | 4.06 | 30 |
| 23.35 | 3.81 | 70 |
| 24.40 | 3.65 | 42 |
| 24.67 | 3.61 | 58 |
| 26.36 | 3.38 | 28 |
| 29.46 | 3.03 | 25 |
| 31.60 | 2.83 | 23 |

More preferably, the crystalline HCl salt of compound (I-C) is characterized by its powder XRD pattern, which comprises peaks having a relative intensity greater than or equal to about 25%, more preferably greater than or equal to about 50%.

The present invention further comprises pharmaceutical compositions containing one or more compounds prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1,000 mg or any range therein, and may be given at a dosage of from about 0.01-100 mg/kg/day, or any range therein, preferably from about 0.01-50 mg/kg/day, or any range therein, more preferably from about 0.01-10 mg/kg/day, or any range therein, more preferably from about 0.05-1 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, or any range therein, for example at 1 mg, 5 mg, 10 mg, 25 mg, 30 mg, 50 mg, 75 mg, 100 mg, or any amount therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating described in the present invention may also be carried out using a pharmaceutical composition comprising any of the compounds as defined herein and a pharmaceutically acceptable carrier. The pharmaceutical composition may contain between about 0.1 mg and 1000 mg of the compound, or any range therein; preferably about 0.01 to 10 mg of the compound, or any range therein, more preferably about 0.01 to 1 mg of the compound, or any range therein, more preferably about 0.01 to about 0.05 mg, or any range thereof, and may be constituted into any form suitable for the mode of administration selected. Carriers include necessary and inert pharmaceutical excipients, including, but not limited to, binders, suspending agents, lubricants, flavourants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methylcellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets. Second Edition. Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of diseases, disorders or conditions modulated by the histamine H3 receptor is required.

The daily dosage of the products may be varied over a wide range from 0.1 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any range therein. Preferably, the range is from about 0.01 to about 50.0 mg/kg of body weight per day, or any range therein. More preferably, from about 0.01 to about 10.0 mg/kg of body weight per day, or any range therein. More preferably, from about 0.01 to about 1.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

(6-Chloro-pyridin-3-yl)-[1,4]diazepan-1-yl-methanone

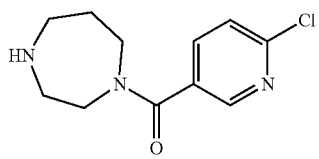 [SMILES: O=C(c1ccc(Cl)nc1)N1CCCNCC1]

A solution of homopiperazine (385.62 g, 3.85 mol) in THF (3.9 L) was cooled to an internal temperature of 0° C. and ethyl 6-chloronicotinate (285.82 g, 1.54 mol) was added in THF (0.57 L) over 5 min. After stirring for 10 minutes, n-hexyl lithium (2.3 M in hexane, 335 mL, 0.77 mol) was added to the resulting mixture, over 40 min. The resulting mixture was stirred for 2 h at 000° C., then warmed to 20° C. over 1 h. After an additional 15h at 20° C., the resulting mixture was treated with 1M NaOAc/HOAc buffer (5 L) (prepared by diluting 47.35 g of sodium acetate and 253.2 mL of acetic acid with water to a total volume of 5 L). The resulting layers were separated and the aqueous layer pH was then increased from 8.0 to 11.35 with 50% $NaOH_{(aq)}$ solution (153 mL). The basic layer was extracted with dichloromethane (2×4 L) and the resulting organics dried with sodium sulfate, filtered, and concentrated to yield a thick oil.

$^1$H-NMR: (400 MHz, $CDCl_3$) δ, 8.46-8.45 (m, 1H), 7.75-7.72 (m, 1H), 7.40-7.38 (m, 1H), 3.80-3.75 (m, 2H), 3.49-3.44 (m, 2H), 3.09-3.06 (m, 1H), 2.96-2.89 (m, 3H), 1.95-1.88 (m, 1H), 1.75-1.70 (m, 1H)

MS (electrospray): exact mass calculated for $C_{11}H_{14}ClN_3O$, 239.08; m/z found, 240.1 [M+H]+.

Example 2

(6-Chloro-pyridin-3-yl)-[1,4]diazepan-1-yl-methanone

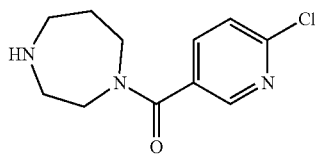

A solution of homopiperazine (12.5 g, 125 mmol) and ethyl-6-chloronicotinate (9.28 g, 50 mmol) in THF (150 mL) was cooled to 0° C. and LiOEt (1 M in THF, 50 mL, 50 mmol) was then added over 20 minutes. The resulting mixture was stirred at 0° C. for 2 h, then warmed to 20° C. and held at this temperature for 17 h. The resulting mixture was then treated with 162 mL of an aqueous solution containing 1.53 g of NaOAc and 8.2 mL of acetic acid. The resulting layers were separated and the organic was diluted with hexane (50 mL) and extracted again with the same aqueous solution as utilized above. The aqueous pH was then increased to 10 through addition of 50% $NaOH_{(aq)}$ (15 mL). After extraction with dichloromethane (3×250 mL) the combined organics were dried over sodium sulfate, filtered, and concentrated to yield the title compound as an oil.

Example 3

(6-Chloro-pyridin-3-yl)-(4-cyclobutyl-[1,4]diazepan-1-yl)-methanone

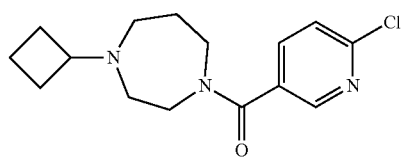 [SMILES: O=C(c1ccc(Cl)nc1)N1CCCN(C2CCC2)CC1]

To a solution of (6-chloro-pyridin-3-yl)-[1,4]diazepan-1-yl-methanone (255.1 g, 1.06 mol) in dichloroethane (3.0 L) was added cyclobutanone (108.1 mL, 1.45 mol). After a 1 h aging period, sodium triacetoxyborohydride (308.2 g, 1.45 mol) was added in four equal portions over 1.5 h. The resulting mixture was allowed to stir for 20 h, then quenched with 2.5 L of an aqueous solution containing NaOH (141.3 g, 3.53 mol). After stirring for 30 minutes, the layers were separated and the organic dried with magnesium sulfate, filtered, and concentrated to yield the title compound as an oil.

Example 4

Purification of (6-Chloro-pyridin-3-yl)-4-cyclobutyl-[1,4]diazepan-1-yl)-methanone The oil prepared as in Example 4 above was purified through formation of the corresponding tartrate salt as follows.

To the (6-chloro-pyridin-3-yl)-(4-cyclobutyl-[1,4]diazepam-1-yl)-methanone (311.5 g actual desired, 1.06 mol) oil in ethanol (3.0 L) was added L-tartaric acid (167.05 g, 1.11 mol). The resulting heterogeneous suspension was warmed to 80° C. over 45 minutes and held for 1 h. The resulting mixture was then cooled to 20° C. over 3 h and stirred at 20° C. for 1 h. The resulting solids were filtered and washed with ethanol (1 L). The resulting material was dried under vacuum at 43° C. to yield an off-white solid, the corresponding tartaric acid salt or (6-chloro-pyridin-3-yl)-(4-cyclobutyl-[1,4]diazepam-1-yl)-methanone.

A portion of the tartrate salt was then reacted to yield the (6-chloro-pyridin-3-yl)-(4-cyclobutyl-[1,4]diazepam-1-yl)-methanone free base as follows.

A mixture of (6-chloro-pyridin-3-yl)-(4-cyclobutyl-[1,4]diazepan-1-yl)-methanone*L-tartaric acid (172 g, 386.9 mmol), iPrOAc (1.5 L), and 1 N $NaOH_{(aq)}$ (1.5 L) was thoroughly mixed and the resulting layers were separated. The aqueous layer was extracted with additional iPrOAc (1.5 L) and the combined organic layers were dried over magnesium sulfate. After filtration and concentration, (6-chloro-pyridin-3-yl)-(4-cyclobutyl-[1,4]diazepam-1-yl)-methanone was obtained as a yellow oil.

$^1$H-NMR: (400 MHz, $CDCl_3$) δ, 8.46-8.45 (m, 1H), 7.75-7.72 (m, 1H), 7.40-7.38 (m, 1H), 3.80-3.75 (m, 2H), 3.49-3.44 (m, 2H), 3.09-3.06 (m, 1H), 2.96-2.89 (m, 3H), 1.95-1.88 (m, 1H), 1.75-1.70 (M, 1H)

MS (electrospray): exact mass calculated for $C_{11}H_{14}ClN_3O$, 239.08; m/z found, 240.1 [M+H]+.

Example 5

3-[5-(4-Cyclobutyl-[1,4]diazepane-1-carbonyl)-pyridin-2-yloxy]-benzonitrile

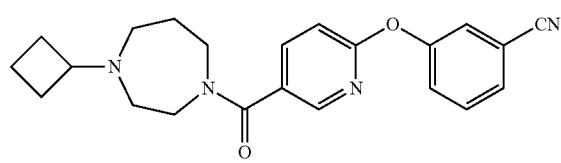 [SMILES: N#Cc1cccc(Oc2ccc(C(=O)N3CCCN(C4CCC4)CC3)cn2)c1]

To a solution of (6-chloro-pyridin-3-yl)-(4-cyclobutyl-[1,4]diazepan-1-yl)-methanone (101.0 g, 343.8 mmol) in dimethylacetamide (1.1 L) was added $Cs_2CO_3$ (224 g, 687.6 mmol) and m-cyanophenol (81.9 g, 687.6 mmol). The resulting mixture was warmed to 125° C. and stirred for 20 h. After cooling to room temperature, the resulting mixture was filtered and acetic acid (1.5 L) was added to the filtrate. The resulting mixture was concentrated under reduced pressure to yield a brown residue which was taken up into MTBE (1.5 L) and 1N $NaOH_{(aq)}$ (1.5 L). The resulting layers were thoroughly mixed and then separated. The organic extract was dried over magnesium sulfate, filtered, and concentrated to yield the title compound as a brown oil.

$^1$H-NMR: (400 MHz, $CDCl_3$) δ, 8.22 (s, 1H), 7.84 (dd, J=8.4, 2.4 Hz, 1H), 7.55-7.37 (m, 4H), 7.03 (d, J=8.4 Hz, 1H), 3.77 (m, 2H), 3.53 (m, 2H), 2.98-2.8 (m, 1H), 2.70-2.58 (m, 1H), 2.55-2.35 (m, 3H), 2.15-1.53 (m, 8H)

MS (electrospray): exact mass calculated for $C_{22}H_{24}N_4O_2$, 376.19; m/z found, 377.2 [M+H]+.

Example 6

3-[5-(4-Cyclobutyl-[1,4]diazepane-1-carbonyl)-pyridin-2-yloxy]-benzonitrile.HCl

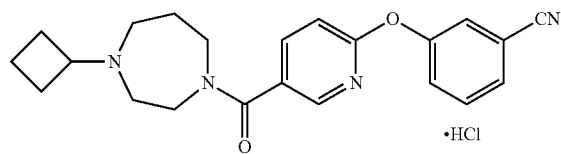 [SMILES: N#Cc1cccc(Oc2ccc(C(=O)N3CCCN(C4CCC4)CC3)cn2)c1 ; Cl]

A slurry of 3-[5-(4-cyclobutyl-[1,4]diazepane-1-carbonyl)-pyridin-2-yloxy]-benzonitrile (10.4 g, 27.6 mmol) in isopropanol (80 mL) was warmed to 50° C. To the resulting solution was added anhydrous HCl (5.54 mL, 5 M HCl in IPA, 27.7 mmol). The resulting mixture was cooled to 20° C. over 1 h, and then held at 20° C. for 20 h. The resulting slurry was filtered, washed with isopropanol, and dried at 50° C. in a vacuum oven to yield the title compound as an off-white crystalline solid.

Example 7

3-[5-(4-Cyclobutyl-[1,4]diazepane-1-carbonyl)-pyridin-2-yloxy]-benzonitrile.HCl

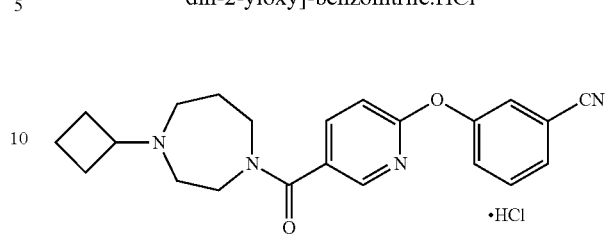

A solution of 3-[5-(4-cyclobutyl-[1,4]diazepane-1-carbonyl)-pyridin-2-yloxy]-benzonitrile (114 g, 302.8 mmol) in IPA (900 mL) was warmed to 40° C. To the resulting solution was added anhydrous HCl (5-6 M solution in IPA, 60.6 mL, 302.8 mmol). After the addition of seed crystals (which may be prepared for example, as described in Example 6 above), the resulting mixture was cooled to 35° C. and held for two hours. The resulting mixture was cooled to room temperature, filtered, washed with IPA (220 mL), and the isolated residue dried at 50° C. to yield the title compound as an off-white crystalline solid.

$^1$H-NMR: (400 MHz, DMSO) δ, 11.45 (bs, 1H), 8.29 (bs, 1H), 8.01 (bd, J=7.8 Hz, 1H), 7.82-7.5 (m, 4H), 7.2 (d, J=8.5 Hz, 1H), 4.1 (m, 1H), 3.8-3.3 (m, 6H), 3.1-2.8 (m, 2H), 2.49-2.25 (m, 3H), 2.25-1.9 (m, 3H), 1.8-1.55 (m, 2H)

Example 8

(4-Cyclobutyl-[1,4]diazepan-1-yl)-[6-(tetrahydro-pyran-4-yloxy)-pyridin-3-yl]-methanone

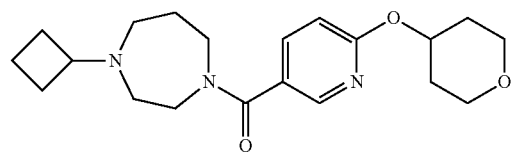 [SMILES: O=C(c1ccc(OC2CCOCC2)nc1)N1CCCN(C2CCC2)CC1]

To a solution of (6-chloro-pyridin-3-yl)-(4-cyclobutyl-[1,4]diazepan-1-yl)-methanone (32.7 g, 111.3 mmol) in toluene (470 mL) was added tetrahydro-pyran-4-ol (13.6 g, 133.6 mmol), 18-crown-6 (1.47 g, 5.565 mmol), and then KOH (pulverized solid, 20.6 g, 367.3 mmol). The resulting heterogeneous mixture was warmed to 110° C. and stirred for 3 h. After cooling to room temperature, water (470 mL) was added and the resulting layers were thoroughly mixed and then separated. The organic extract was dried over magnesium sulfate, filtered, and concentrated to yield the title compound as a yellow oil.

$^1$H-NMR: (400 MHz, $CDCl_3$) δ, 8.21 (s, 1H), 7.65 (dd, J=8.5, 2.4 Hz, 1H), 6.73 (dd, J=8.5, 0.6 Hz, 1H), 5.31-5.21 (m, 1H), 4.02-3.94 (m, 2H), 3.78-3.72 (m, 2H), 3.61 (ddd, J=11.9, 9.1, 2.9 Hz, 2H), 3.57-3.49 (m, 2H), 2.96-2.80 (m, 1H), 2.66-2.58 (m, 1H), 2.54-2.40 (m, 3H), 2.11-1.91 (m, 5H), 1.90-1.73 (m, 5H), 1.71-1.56 (m, 2H)

MS (electrospray): exact mass calculated for $C_{20}H_{29}N_3O_3$, 359.22; m/z found, 360.2 [M+H]+.

Example 9

(4-Cyclobutyl-[1,4]diazepan-1-yl)-[6-(tetrahydro-pyran-4-yloxy)-pyridin-3-yl]-methanone.HCl

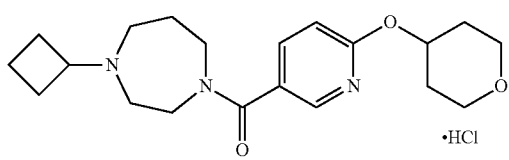 [SMILES: O=C(c1ccc(OC2CCOCC2)nc1)N1CCCN(C2CCC2)CC1 ; Cl]

To a solution of (4-cyclobutyl-[1,4]diazepam-1-yl)-[6-(tetrahydro-pyran-4-yloxy)-pyridin-3-yl]-methanone (200 mg, 0.56 mmol) in isopropanol (1.5 mL) was added anhydrous HCl (112 µL, 5 M HCl in IPA, 0.56 mmoL). The resulting slurry was warmed to 80° C. and then cooled to 45° C. and stirred overnight. After further cooling to room temperature, the title compound was isolated as a white crystalline solid.

Example 10

(4-Cyclobutyl-[1,4]diazepan-1-yl)-[6-(tetrahydro-pyran-4-yloxy)-pyridin-3-yl]-methanone.HCl

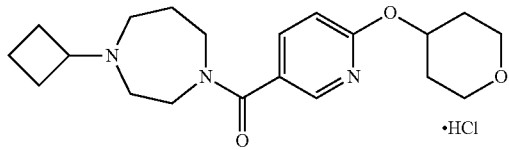 [SMILES: O=C(c1ccc(OC2CCOCC2)nc1)N1CCCN(C2CCC2)CC1 ; Cl]

To a solution of (4-cyclobutyl-[1,4]diazepan-1-yl)-[6-(tetrahydro-pyran-4-yloxy)-pyridin-3-yl]-methanone (6.17 g, 17.2 mmol) in IPA (100 mL) was added anhydrous HCl (5-6 M solution in IPA, 3.44 mL, 17.2 mmol). The resulting mixture was then warmed to 80° C. and then cooled to 60° C. to promote precipitation. Seed crystals (which may be prepared for example, as described in Example 9 above) were added at this point. The resulting mixture was cooled to room temperature, filtered, washed with IPA (50 mL), and dried at 50° C. to yield the title compound as its corresponding HCl salt, as a white crystalline solid.

$^1$H-NMR: (400 MHz, DMSO) δ, 11.46 (bs, 1H), 8.29 (bs, 1H), 7.82 (bd, J=7.6 Hz, 1H), 6.86 (d, J=8.8 Hz, 1H), 5.22 (m, 1H), 4.18-3.22 (m, 11H), 3.10-2.90 (m, 2H), 2.48-2.25 (m, 3H), 2.25-1.97 (m, 5H), 1.78-1.59 (m, 4H)

Elemental Analysis for $C_{20}H_{30}ClN_3O_3$: Calculated: C, 60.67; H, 7.64; N, 10.61; Cl, 8.95; Measured: C, 60.71; H, 7.90; N, 10.50; Cl, 8.88

Example 11

(4-Cyclobutyl-[1,4]diazepam-1-yl)-[6-(4-fluoro-phenoxy)-pyridin-3-yl]-methanone

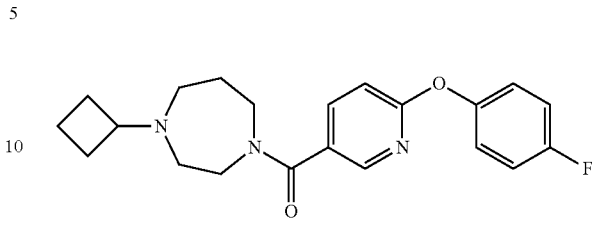

A mixture of (6-chloro-pyridin-3-yl)-(4-cyclobutyl-[1,4]diazepan-1-yl)-methanone (308 mg, 1.05 mmol), cesium carbonate (683 mg, 2.1 mmol), 4-fluorophenol (235 mg, 2.1 mmol), and N,N-dimethylacetamide (5 mL) was heated at 110° C. for 15 h. The resulting mixture was then cooled, filtered, and diluted with acetic acid (10 mL). The resulting solution was concentrated under reduced pressure and then partitioned between MTBE (10 mL) and 1N NaOH$_{(aq)}$ (10 mL). The organic layer was diluted with dichloromethane, washed with water and concentrated to yield the title compound as a yellow oil.

$^1$H-NMR: (400 MHz, CDCl3) δ, 8.23 (d, J=2.1 Hz, 1H), 7.78 (dd, J=8.5, 2.4, 1H), 7.15-7.05 (m, 4H), 6.94 (dd, J=8.4, 0.6 Hz, 1H), 3.82-3.7 (m, 2H), 3.6-3.45 (m, 2H), 2.95-2.8 (m, 1H), 2.65-2.57 (m, 1H), 2.55-2.4 (m, 3H), 2.1-1.55 (m, 8H)

Example 12

Homopiperazine-Cyclobutylaminal

Under a nitrogen atmosphere, homopiperazine (also known as [1,4]-diazepane, 30.05 g, 0.3 mol, 1 eq) was dissolved in toluene (150 g). To the resulting solution was added cyclobutanone (21.03 g, 0.3 mol, 1 eq). The resulting mixture was heated to ~80-87° C., 1000 mbar for 2 hours and then at ~90-125° C., 800 mbar for 2 hours. The water formed as a result of the reaction removed by means of a Dean-Stark apparatus (~5.4 g). The residual solvent was then distilled off to yield a residue, the title compound as an orange oil. The oil was used in subsequent steps without further purification.

Example 13

1-Cyclobutyl-[1,4]diazepane

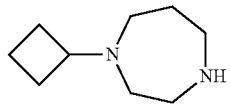

Under a nitrogen atmosphere, 32% aqueous hydrochloric acid (227.9 g, 2 mol, 4 eq) was cooled to a temperature in the range of −5° C. to 0° C. Homopiperazine-cyclobutylaminal prepared as in Example 12 above (89.6 g, 0.5 mol), was added dropwise while maintaining the internal temperature of the reaction mixture at −5° C. to 0° C. (about 1-2 hours). To the resulting mixture was then added a solution of sodium borohydride (18.9 g, 0.5 mol, 1 eq) in water (37.5 g) stabilized with sodium hydroxide (6.7 g, 30% NaOH$_{(aq)}$, 0.05 mol, 0.1 eq) while maintaining the temperature of the reaction mixture at −2° C. to 2° C. (about 2-3 hours). After the addition, the resulting mixture was warmed to 20-25° C. and stirred overnight. The resulting mixture was then neutralized with 30% sodium hydroxide (273.4 g, 2.05 mol, 2.01 eq) and then extracted with MTBE (3×111 g). The organic layers were combined, the resulting suspension was filtered and the flask and filter cake washed with MTBE (14.8 g). Any remaining residual solvent was removed to yield the title compound as a yellowish oil, which was used in subsequent steps without further purification.

Example 14

(6-Chloro-pyridin-3-yl-(4-cyclobutyl-[1,4]diazepan-1-yl)-methanone HCl salt

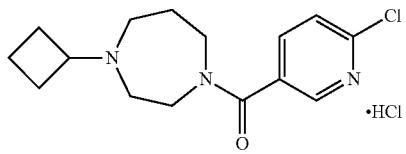 [SMILES: O=C(c1ccc(Cl)nc1)N1CCCN(C2CCC2)CC1 ; Cl]

6-Chloronicotinic acid chloride (25.0 g, 137.8 mmol, 1 eq) was dissolved in 2-methyl-THF (328.0 g). A solution of 1-cyclobutyl-[1,4]diazepane (prepared as in Example 13 above, 24.1 g, 147.8 mmol, 1.05 eq) in 2-methyl-THF (164.0 g) was then added to the reaction mixture, while maintaining the temperature of the reaction mixture at less than 35° C. (about 45 min-1.5 hours). The resulting suspension was stirred at room temperature for 16 hours, then cooled to about 0-5° C. and maintained at 0° C. for 2 hours. The title compound was isolated by filtration, washed with 2-methyl-THF (2×45.0 g), then dried in vacuo at 60° C., to yield the title compound as a white solid.

Example 15

(6-Chloro-pyridin-3-yl)-(4-cyclobutyl-[1,4]diazepan-1-yl)-methanone HCl (Direct Coupling)

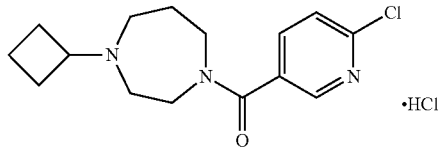 [SMILES: O=C(c1ccc(Cl)nc1)N1CCCN(C2CCC2)CC1 ; Cl]

To a suspension of 95% sodium triacetoxyborohydride (4.34 g, 19.45 mmol) in THF (30.0 g) was added a solution of homopiperazine-cyclobutylaminal (2.70 g, 17.74 mmol) in THF (5.4 g) at about 20-25° C. and the resulting mixture stirred for 1 hour. To the resulting mixture was then added 97% 6-chloronicotinic acid chloride (3.0 g, 16.53 mmol) in THF (12.0 g) and the resulting mixture stirred at room temperature for 1 hour. Excess sodium triacetoxyborohydride was then quenched with water (5.0 g). After stirring 15 minutes, 10% NaOH$_{(aq)}$ (16.5 g) was added and the mixture stirred for 25 minutes. The resulting layers were separated, the organic layer washed with brine (10.5 g). The organic layer was again separated and filtered. To the organic layer was then added toluene (16.2 g), part of the solvent distilled off at 220 mbar, 45° C. At 38° C., 6N HCl in isopropanol was added dropwise, resulting in the formation of two layers. Additional isopropanol was added (2.6 g). The solvent was then completely removed to yield a yellowish foam residue. The residue was dissolved in ethanol (12.0 g) and MTBE (50 g) added, resulting in the formation of a precipitate. The resulting mixture was heated to 50° C., cooled slowly to room temperature and stirred overnight. The title compound was isolated by filtration, washed with MTBE (2×20 g, 1×10 g) and dried in vacuo at 45° C. to yield a white solid.

Example 16

(4-Cyclobutyl-[1,4]diazepan-1-yl)-[6-(tetrahydro-pyran-4-yloxy)-pyridin-3-yl]-methanone.HCl

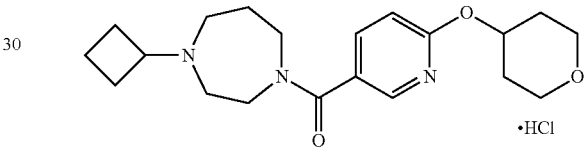

(6-Chloro-pyridin-3-yl)-(4-cyclobutyl-[1,4]diazepan-1-yl)-methanone (20.0 g, 51 mmol), sodium carbonate (8.0 g, 75.5 mmol), water (72.0 g) and toluene (100.0 g) were mixed for 30 minutes at room temperature. The resulting biphasic mixture was separated and the aqueous layer removed. The remaining organic layer was concentrated in vacuo to yield a yellow oil (14.97 g). Tetrahydropyran-4-ol (6.24 g, 61.1 mmol), potassium hydroxide (4.75 g, 84.7 mmol) and toluene (200 g) were added, the resulting mixture heated to reflux and the water formed in the reaction removed with a Dean-Stark apparatus. The resulting mixture was cooled to 20-30° C. and water (80.0 g) was added. The resulting mixture was stirred for 10 min, the layers allowed to separate and the aqueous layer removed. The organic layer was slightly concentrated to remove any traces of water, then treated with a mixture of 6N HCl in isopropanol (10.98 g, 61.2 mmol) and toluene (70 g) at 60-70° C. The resulting suspension was maintained at 60° C. for 1 hour, then cooled to 0-5° C. over about 3 hours, then maintained at 00° C. for 30 min. The precipitate was isolated by filtration, washed with toluene (2×10 g) and dried in vacuo to yield the title compound as a white solid.

Recrystallization:
The white solid prepared above (13.5 g, 34.1 mmol) was dissolved in isopropanol (265.0 g) at reflux. The resulting mixture was cooled to 55-65° C. over about 40 min, during which time crystallization slowly set in. The resulting mixture was maintained at 55-65° C. for 2 hours, then cooled to room temperature and held overnight. The resulting mixture was re-heated to 45° C., and held at this temperature for 2.5 hours. The resulting suspension was then cooled to 0-5° C. over about 1.5 hours and then held at this temperature for 1 hour. The title compound was isolated by filtration, washed with isopropanol (2×15 g), dried in vacuo at 75-100° C. to yield a white solid.

Example 17

3-[5-(4-Cyclobutyl-[1,4]diazepane-1-carbonyl)-pyridin-2-yloxy]-benzonitrile

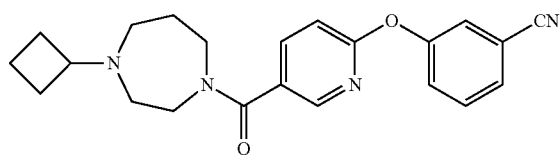 [SMILES: N#Cc1cccc(Oc2ccc(C(=O)N3CCCN(C4CCC4)CC3)cn2)c1]

A reactor was charged with (6-chloro-pyridin-3-yl)-(4-cyclobutyl-[1,4]diazepam-1-yl-methanone hydrochloride (20.0 g, 60.6 mmol), 3-hydroxybenzonitrile (10.8 g, 90.7 mmol), cesium carbonate (52.5 g, 151.6 mmol), acetonitrile (62.6 g) and dimethylacetamide (50.0 g). The resulting yellowish suspension was heated to reflux (95° C.) over about 15 min and maintained at reflux for 65 min. The acetonitrile was then distilled off, until the temperature had risen to about 105-110° C. The resulting mixture was then stirred at 105-110° C. for 5 hours, then cooled to 20° C. and held at this temperature overnight. The resulting mixture was then re-heated to reflux for another 4 hours, 15 min, then cooled to 65° C., the cesium salts were removed by filtration and the filter cake washed with acetonitrile (20.5 g) via the reactor. To the filtrate was added water (60.1 g), then acetonitrile was removed by distillation in vacuo (50-55° C., 250-70 mbar). The resulting residue was extracted twice with MTBE (65.0 g, respectively) at 45° C. The combined organic layers were washed with 2 N NaOH$_{(aq)}$ (20 g) and water (2×20 g) at 45° C. Approximately 50% of the solvent was then distilled off from the organic layer and some seed crystals of the desired product crystalline form were added. The resulting mixture was then cooled to room temperature over about 2.5 hours, and held at this temperature overnight. The resulting mixture was heated to 35° C., and cyclohexane (100.0 g) was added over about 1.5 hours. The resulting, thick, slightly pink suspension was held at 35° C. for 1 hour, then cooled to 15° C. over about 2 h, held at 15° C. for 2 hours, cooled to 0° C. over about 1 hour and held at 0° C. for 1 hour, 10 min. The title compound was isolated by filtration, washed with cyclohexane and dried in vacuo at 50° C. to yield an off-white solid.

Example 18

3-[5-(4-Cyclobutyl-[1,4]diazepane-1-carbonyl)-pyridin-2-yloxy]-benzonitrile.HCl

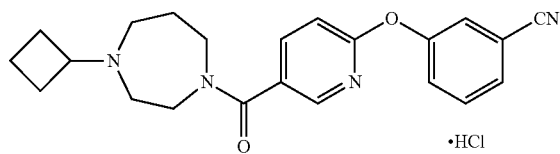 [SMILES: N#Cc1cccc(Oc2ccc(C(=O)N3CCCN(C4CCC4)CC3)cn2)c1 ; Cl]

3-[5-(4-Cyclobutyl-[1,4]diazepane-1-carbonyl)-pyridin-2-yloxy]-benzonitrile (prepared as described in Example 17 above, 14.0 g, 37.2 mmol) was dissolved in ethylmethylketone (112.0 g) and isopropanol (7.0 g) at room temperature. The resulting solution was filtered (absolute filtration), the reactor and filter washed with ethylmethylketone (28.0 g). The resulting solution was then heated to 55-60° C., HCl 37% aq. (2.10 g, 21.3 mmol) was added dropwise over 15 min, and then after 5 min some seeding crystals (0.05 g) of the desired crystalline form were added. The resulting mixture was held at 55-57° C. for 38 min, and then HCl 37% aq. (2.10 g, 21.3 mmol) was added dropwise over 30 min. The resulting white suspension was held at 55-60° C. for 1 hour, 20 min, then cooled to 25° C. over about 3 hours and held at this temperature overnight. The resulting mixture was then cooled to 0-5° C. and held at this temperature for 1.5 hours. The title compound was isolated by filtration, washed with ethylmethylketone (2×28 g) and dried in vacuo at 80° C. to yield a white, crystalline solid.

Example 19

(4-Cyclobutyl-[1,4]diazepam-1-yl)-[6-(4-fluorophenoxy)-pyridin-3-yl]-methanone HCl

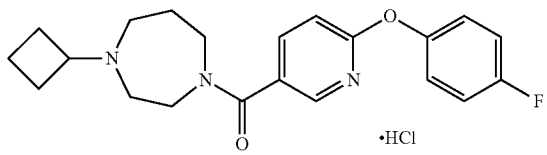 [SMILES: O=C(c1ccc(Oc2ccc(F)cc2)nc1)N1CCCN(C2CCC2)CC1 ; Cl]

A suspension of (6-chloro-pyridin-3-yl)-(4-cyclobutyl-[1,4]diazepam-1-yl-methanone hydrochloride (2.0 g, 5.83 mmol), 4-fluorophenol (1.0 g, 8.92 mmol) and cesium carbonate (5.8 g, 17.8 mmol) in dimethylacetamide (15.0 g) was stirred at 100-110° C. After 4.5 hours, the cesium salts were removed by filtration and the filter cake was washed with t-butylmethylether (3×4.0 g). To the filtrate was added water (15.0 g) and the resulting mixture was stirred for 10 minutes at 40-45° C. The resulting layers were separated, the aqueous layer was washed with twice with t-butylmethylether (12.0 g and 6.0 g, respectively). The organic layers were combined, then washed with 2 N NaOH$_{aq}$ (2.5 g) and water (2×2.5 g). The organic layer was then concentrated (to ~4.5 g) and toluene (10.0 g) added to the resulting residue. To the resulting mixture, at 45° C., 6 N HCl in isopropanol (1.3 g, 7.84 mmol) was then added dropwise. The title compound was observed to precipitate (at first forming as an oil, with the beginning of crystallization after about 10 min). The resulting mixture was stirred at 45° C. for 2 hours, then cooled to 0° C. over about 5 hours, and held at 0° C. for 10 hours. The title compound was isolated by filtration, washed with toluene and dried in vacuo at 55° C. to yield a white solid.

Example 20

(6-Chloro-pyridin-3-yl)-(4-cyclobutyl-[1,4]diazepan-1-yl)-methanone HCl Salt

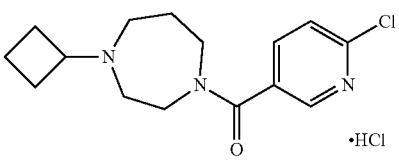 [SMILES: O=C(c1ccc(Cl)nc1)N1CCCN(C2CCC2)CC1 ; Cl]

A mixture of 1-cyclobutyl-[1,4]diazepane (prepared e. g. as in Example 13 above, 20.0 g, 129.7 mmol, 1.00 eq), water (95.2 g) and NaOH 30% aq. (34.6 g, 259.5 mmol, 2.00 eq) was cooled to 10-15° C. To the resulting mixture was added a solution of 6-chloronicotinic acid chloride (24.0 g, 136.4 mmol, 1.05 eq) in MTBE (250.0 g) at 10-15° C., over about 30-45 min, while stirring vigorously. The resulting emulsion was maintained at 10-20° C. for 45-60° C., before the layers were allowed to separate. The aqueous layer was removed and the organic layer washed with water (25.0 g). After removal of the aqueous layer, the organic layer was concentrated by distillation (140 g solvent are distilled off), ethanol (120 g) was added and additional solvent was distilled off (170 g solvent). The resulting solution was then heated to about 50-60° C. and HCl (gas, 4.8 g, 130.2 mmol) in ethanol (9.1 g) was added dropwise. The resulting solution was cooled to 43-45° C. and seeded crystals of the title compound. The product crystallized slowly at 43-45° C. when stirred for about 4-6 h. MTBE (60 g over 1.5-2 h, 120 g over 0.5-1 h) was added, the resulting mixture was then cooled to room temperature over 1-2 h and maintained for 1-2 h, before the title compound was isolated by filtration, washed with MTBE (2× g) and dried in vacuo at 65-75° C. for 2 days, to yield the title compound as a white solid.

Example 21

3-[5-(4-Cyclobutyl-[1,4]diazepane-1-carbonyl)-pyridin-2-yloxy]-benzonitrile.HCl

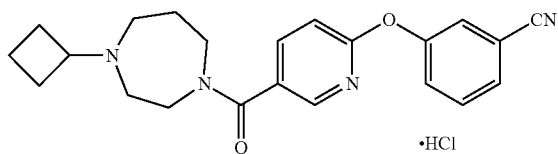 [SMILES: N#Cc1cccc(Oc2ccc(C(=O)N3CCCN(C4CCC4)CC3)cn2)c1 ; Cl]

3-[5-(4-Cyclobutyl-[1,4]diazepane-1-carbonyl)-pyridin-2-yloxy]-benzonitrile.HCl (prepared e. g. as described in Example 18 above, 5.0 g, 12.1 mmol) was slurried in ethanol (15.0 g) at room temperature. The resulting mixture was heated to reflux until the solid had completely dissolved. To the resulting solution was then added 2-propanol (45.0 g) at 70° C. After stirring at 80-85° C. for 20 min, the slightly turbid solution was cooled to 55° C. over 15 minutes and seeding crystals were added. The resulting mixture was kept at 55° C. for 15 min, then it was cooled to 15° C. over 4 h and stirred overnight, resulting in the formation of a thick white suspension. After cooling to 0° C. and stirring for 2 h, the title compound was isolated by filtration, washed with 2-propanol (10 g) and dried in vacuo at 20 to 75° C. to yield a white, crystalline solid. (as FORM II)

Example 22: Oral Formulation (Prophetic Example)

As a specific embodiment of an oral composition, 100 mg of a compound prepared as in Example 20 is formulated with sufficient finely divided lactose to provide a total amount of 580 to 590 mg to fill a size O hard gel capsule.

Example 23: Oral Formulation (Prophetic Example)

As a specific embodiment of an oral composition, 100 mg of a compound prepared as in Example 16 is formulated with sufficient finely divided lactose to provide a total amount of 580 to 590 mg to fill a size O hard gel capsule.

Example 24: Oral Formulation (Prophetic Example)

As a specific embodiment of an oral composition, 100 mg of a compound prepared as in Example 19 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A process for the preparation of a compound of formula (I-E)

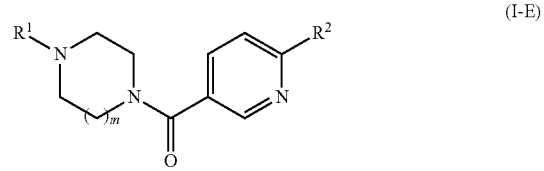

wherein
$R^1$ is selected from the group consisting of $C_{1-4}$alkyl and $C_{3-10}$cycloalkyl;
m is 2
$R^2$ is selected from the group consisting of —OCHR$^3$R$^4$ and —Z—Ar;
$R^3$ is hydrogen and $R^4$ is a $C_{3-10}$cycloalkyl or heterocycloalkyl ring; wherein the $C_{3-10}$ cycloalkyl or the heterocycloalkyl ring is unsubstituted or substituted with —$C_{1-4}$alkyl or acetyl;
alternatively, $R^3$ and $R^4$ are taken together with the carbon to which they are attached to form a $C_{3-10}$cycloalkyl or heterocycloalkyl ring; wherein the $C_{3-10}$cycloalkyl or the heterocycloalkyl ring is unsubstituted or substituted with —$C_{1-4}$alkyl or acetyl;
Z is selected from the group consisting of S and O;
Ar is a phenyl or heteroaryl; wherein the phenyl or heteroaryl is unsubstituted or substituted with one, two, or three $R^5$ substituents; wherein each $R^5$ substituent is independently selected from the group consisting of halogen, —$C_{1-4}$alkyl, —OH, —O$C_{1-4}$alkyl, —S$C_{1-4}$alkyl, —CN, —CONR$^a$R$^b$, and —NO$_2$; and wherein $R^a$ and $R^b$ are each independently —H or —$C_{1-4}$alkyl;
or a pharmaceutically acceptable salt, a pharmaceutically acceptable prodrug, or a pharmaceutically active metabolite thereof; comprising

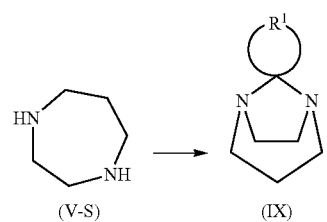

reacting a compound of formula (V-S) with an aldehyde or ketone derivative of the desired R¹ substituent group; neat or in an organic solvent; to yield the corresponding compound of formula (IX);

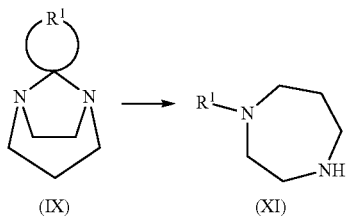

reacting the compound of formula (IX) with a reducing agent; neat, in water or in an aqueous organic solvent; to yield the corresponding compound of formula (XI);

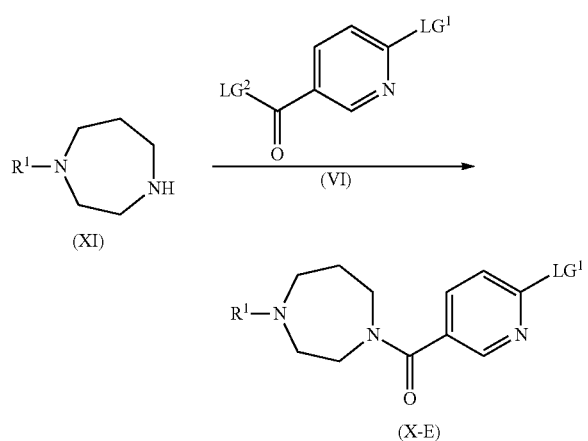

reacting the compound of formula (XI) with a compound of formula (VI), wherein LG¹ is a first leaving group and LG² is a second leaving group; in an organic solvent;

alternatively reacting the compound of formula (XI) with a compound of formula (VI) wherein LG¹ is a first leaving group and LG² is a second leaving group; in the presence of a base; in a mixture of water and an organic solvent;

to yield the corresponding compound of formula (X-E)

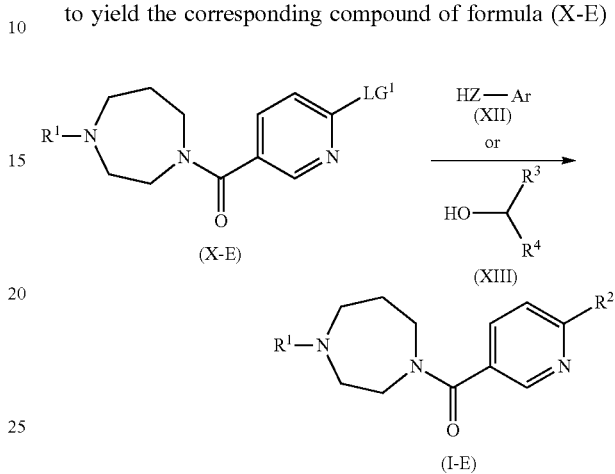

reacting the compound of formula (X-E) with a compound of formula (XII); in the presence of a first inorganic base; in an organic solvent; or reacting the compound of formula (X-E) with a compound of formula (XIII); in the presence of a second inorganic base; in an organic solvent;

to yield the corresponding compound of formula (I-E).

2. A process as in claim 1, wherein R¹ is cyclobutyl; R² is Z—Ar, wherein Ar is selected from the group consisting of 4-fluorophenyl, 3-cyanophenyl, and 4-tetrahydropyranyl; LG¹ is chloro; and LG² is chloro.

* * * * *